(12) United States Patent
Brierton et al.

(10) Patent No.: US 8,443,824 B2
(45) Date of Patent: May 21, 2013

(54) FLUID FLOW CONTROLLER

(75) Inventors: Mark Joseph Brierton, Cary, IL (US); Richard L. West, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 795 days.

(21) Appl. No.: 12/248,343

(22) Filed: Oct. 9, 2008

(65) Prior Publication Data
US 2009/0120505 A1    May 14, 2009

Related U.S. Application Data

(60) Provisional application No. 60/978,613, filed on Oct. 9, 2007, provisional application No. 61/031,894, filed on Feb. 27, 2008, provisional application No. 61/031,995, filed on Feb. 27, 2008, provisional application No. 61/031,811, filed on Feb. 27, 2008.

(51) Int. Cl.
*F16K 17/14* (2006.01)

(52) U.S. Cl.
USPC ........................................ 137/68.21; 137/797

(58) Field of Classification Search
USPC .............. 137/67, 68.11, 68.21, 797; 604/403, 604/905
See application file for complete search history.

(56) References Cited

U.S. PATENT DOCUMENTS

| 4,181,140 A | * | 1/1980 | Bayham et al. ............ 137/68.28 |
| 4,294,247 A | * | 10/1981 | Carter et al. ................. 604/403 |
| 4,340,049 A | * | 7/1982 | Munsch ........................... 604/29 |
| 4,973,328 A |  | 11/1990 | Smith |
| 5,330,464 A | * | 7/1994 | Mathias et al. ............... 604/415 |
| 5,425,920 A |  | 6/1995 | Conti et al. |
| 6,132,413 A |  | 10/2000 | Mathias et al. |
| 6,739,628 B2 | * | 5/2004 | Kanner et al. ...................... 285/4 |
| 7,025,389 B2 |  | 4/2006 | Cuschieri et al. |
| 7,550,185 B2 | * | 6/2009 | Ling et al. ................... 428/36.91 |

FOREIGN PATENT DOCUMENTS

| DE | 9404753 | 5/1994 |
| EP | 1484082 | 12/2004 |
| WO | WO 99/44652 | 9/1999 |

OTHER PUBLICATIONS

European Search Report; EP 08017720 dated Feb. 10, 2009.

* cited by examiner

*Primary Examiner* — Craig Schneider
*Assistant Examiner* — Jessica Cahill
(74) *Attorney, Agent, or Firm* — Cook Alex Ltd.

(57) ABSTRACT

A flow controller includes a housing having central portion and finger-gripping portions on either side of the central portion. The housing defines an interior flow path and includes a breakable member at least partially positioned within the interior flow path of the housing to prevent the passage of fluid through the flow path. The breakable member includes a stem integrally molded to a tubular member. The finger-gripping portions and the central portion define an outermost surface and the outermost surface of the finger gripping portions extends radially outwardly of the outermost surface of the central portion. The central portion includes a wall having a selected thickness.

8 Claims, 27 Drawing Sheets

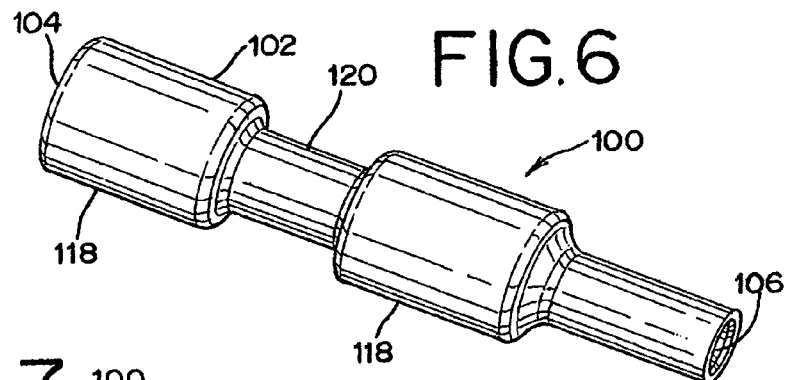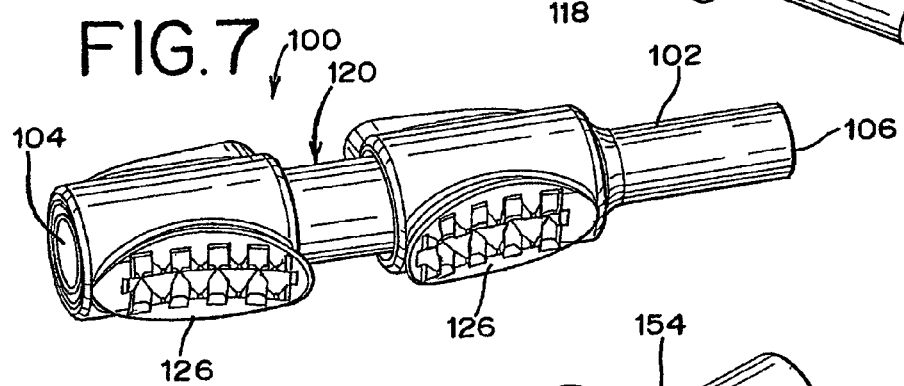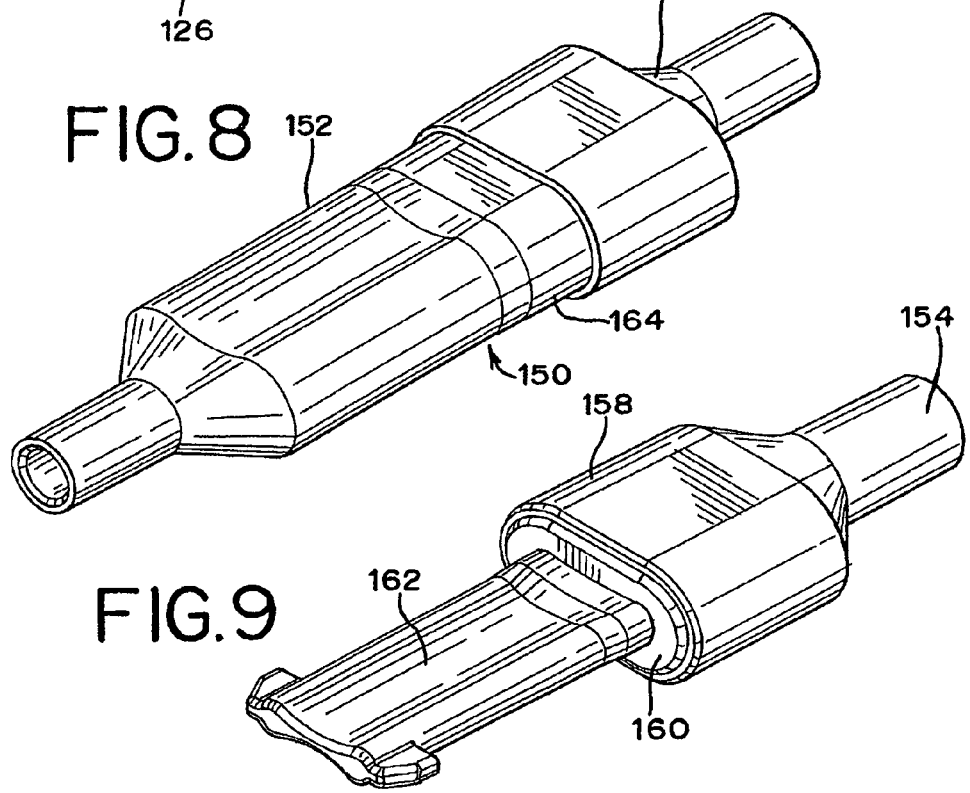

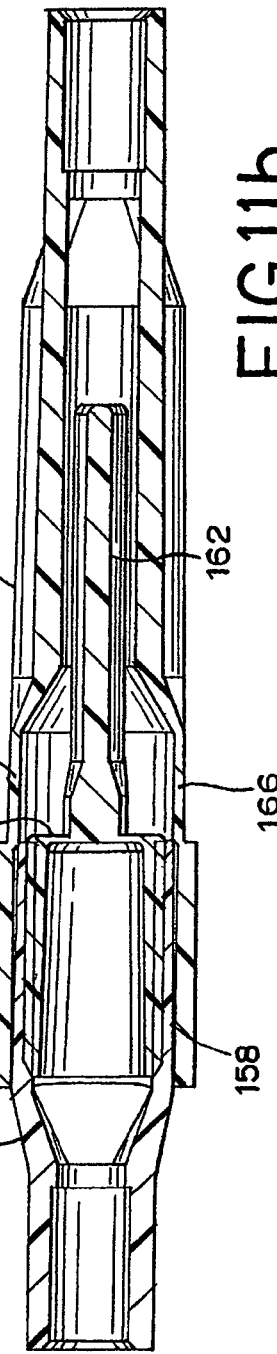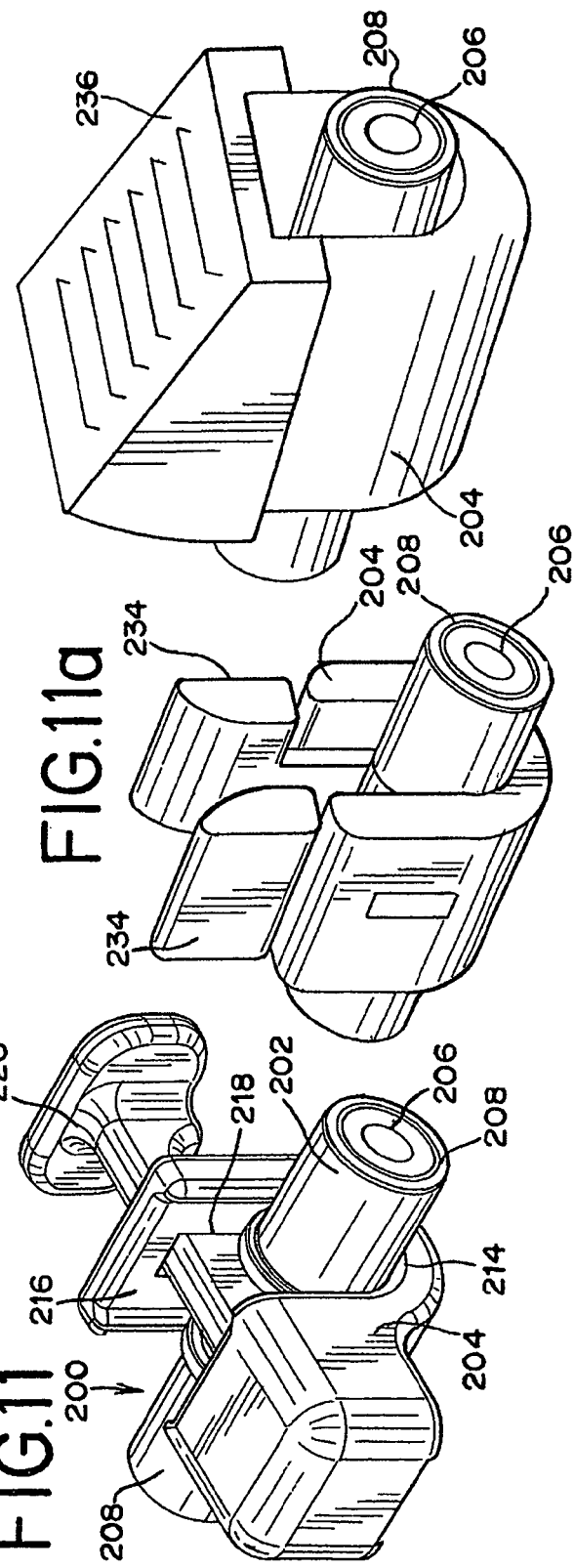

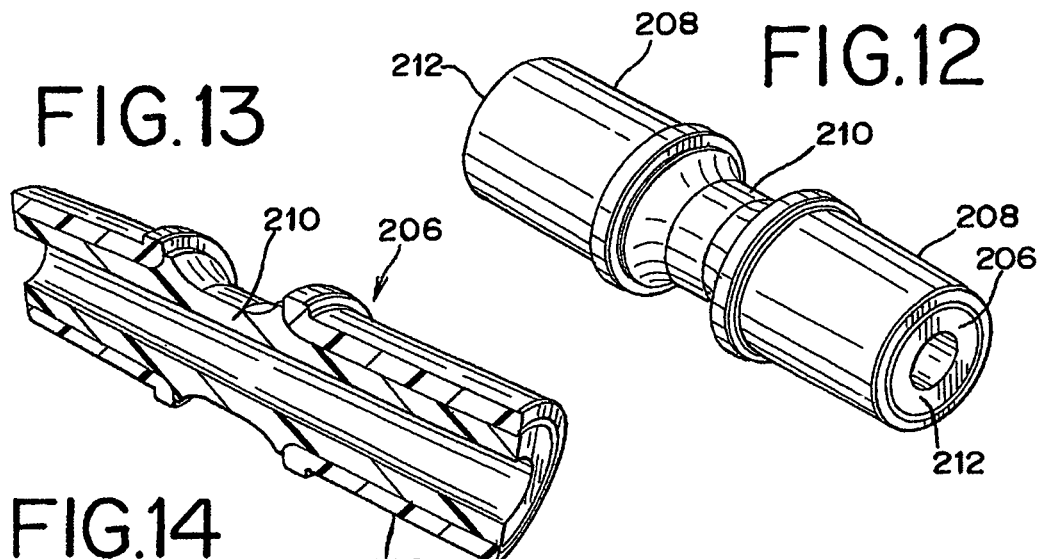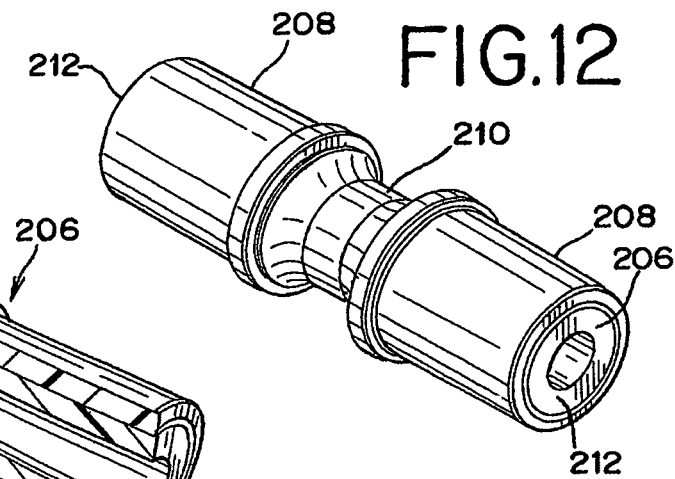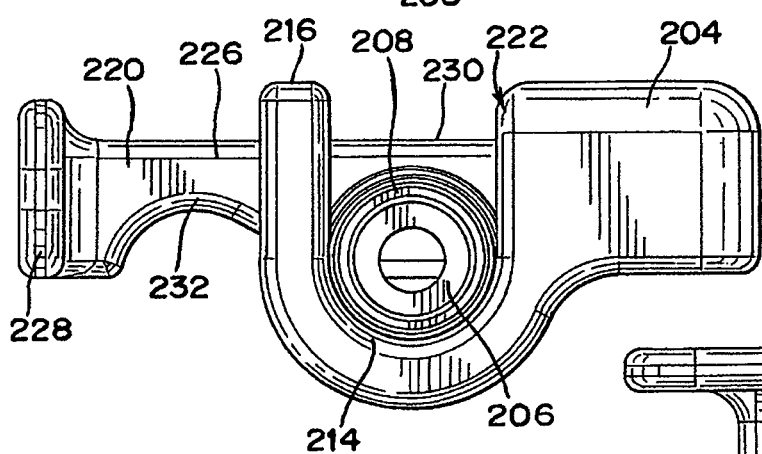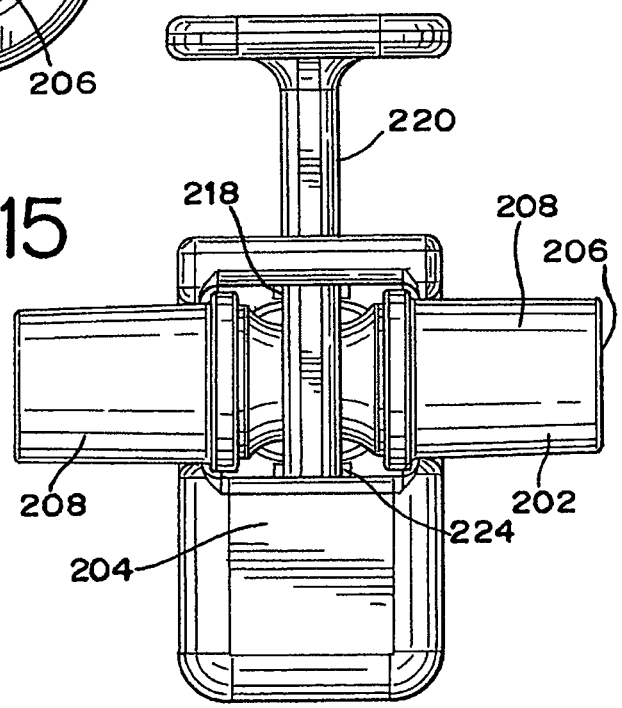

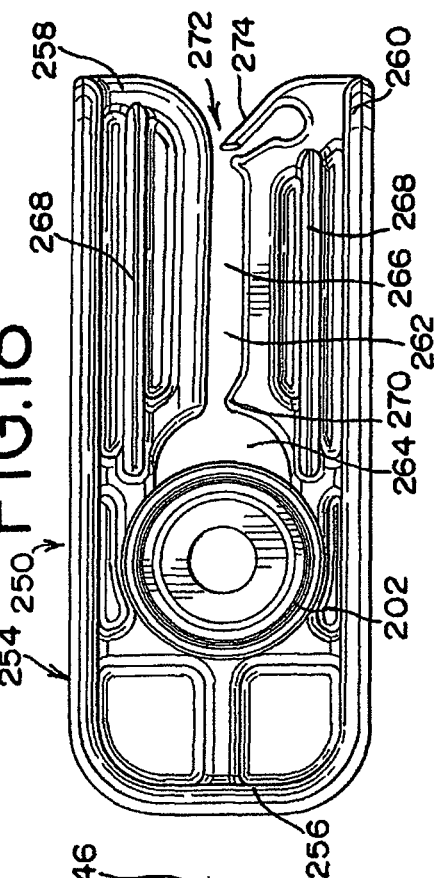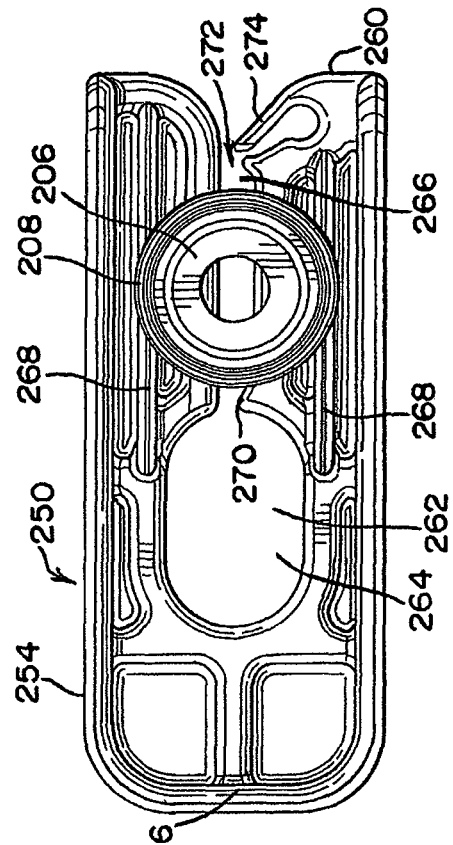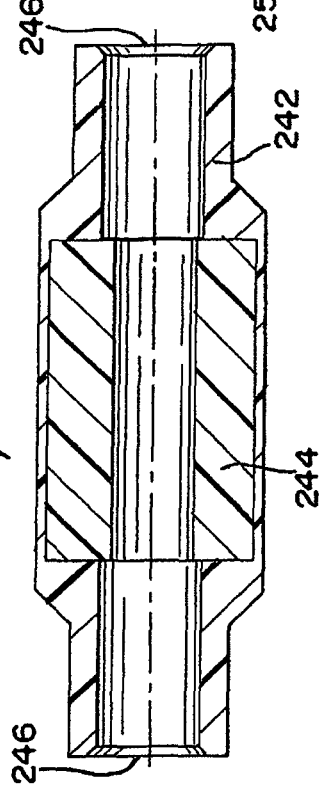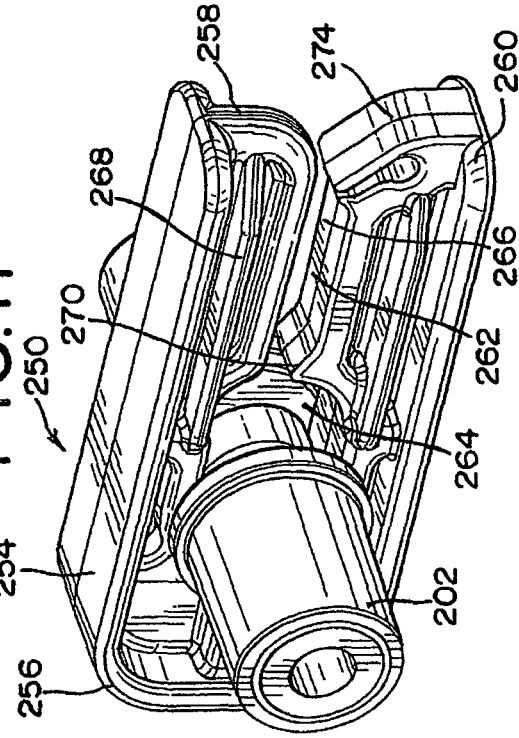

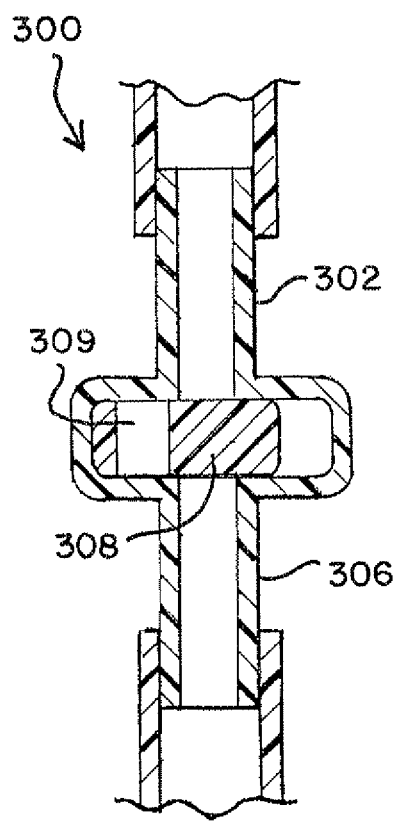
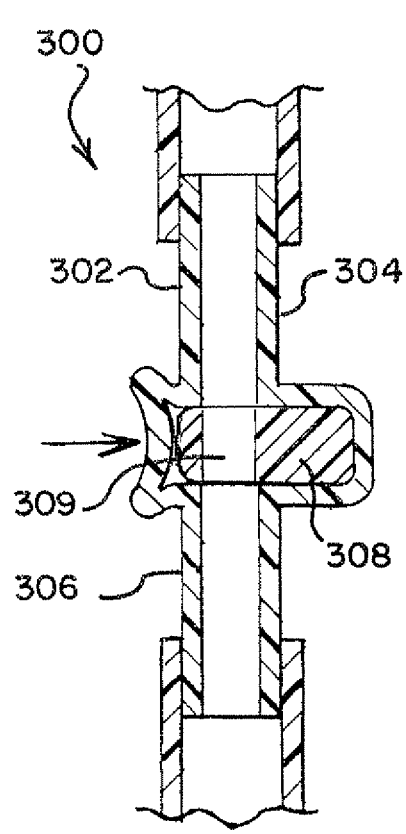

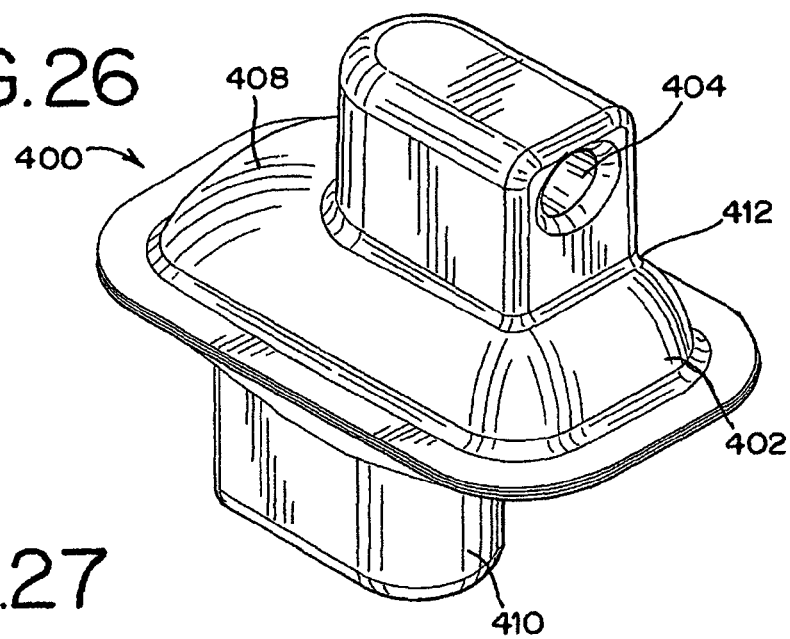
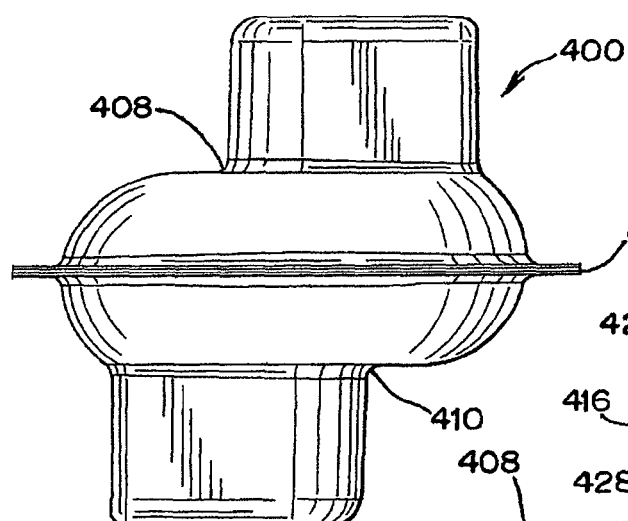
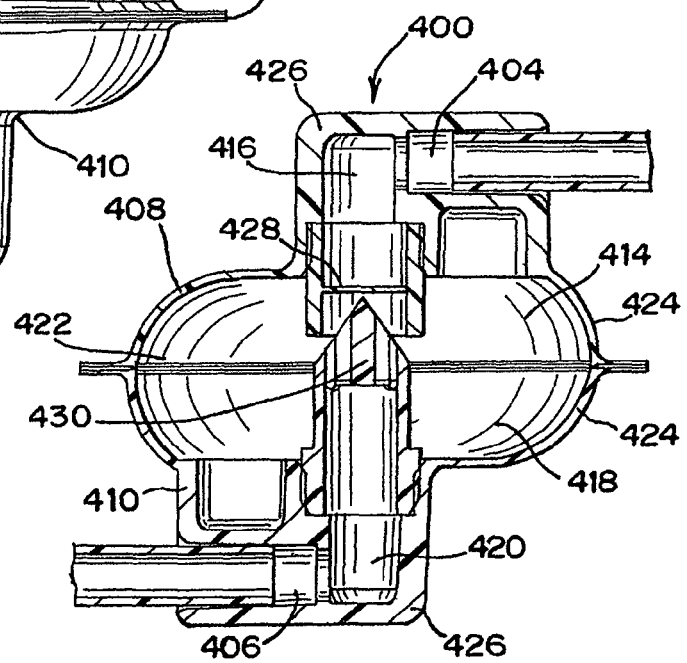

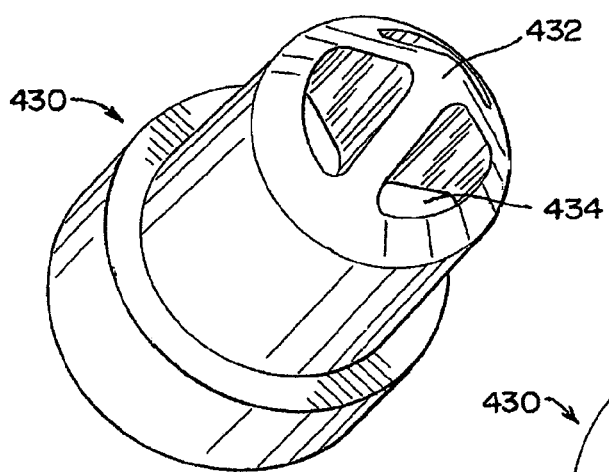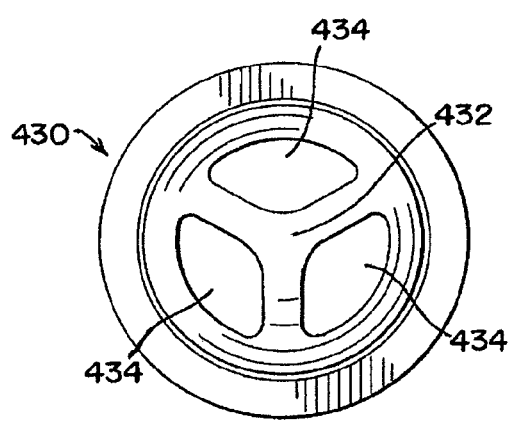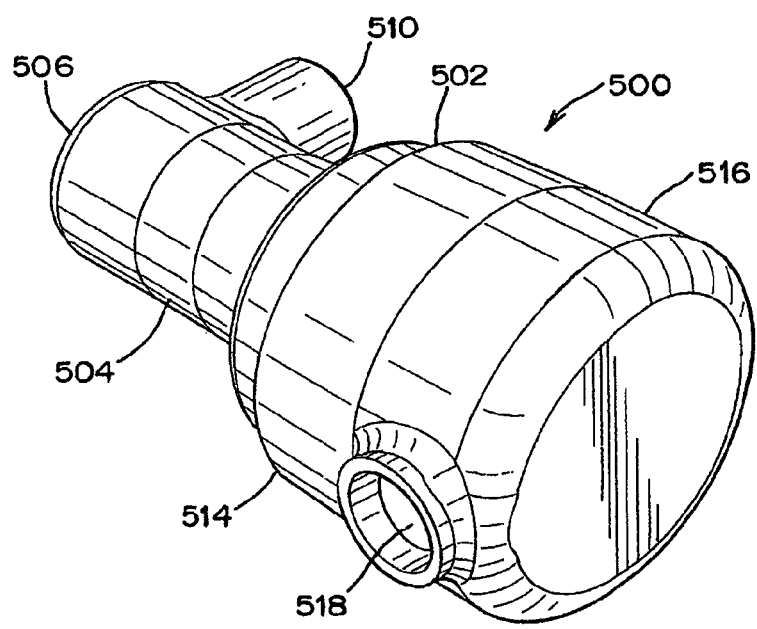

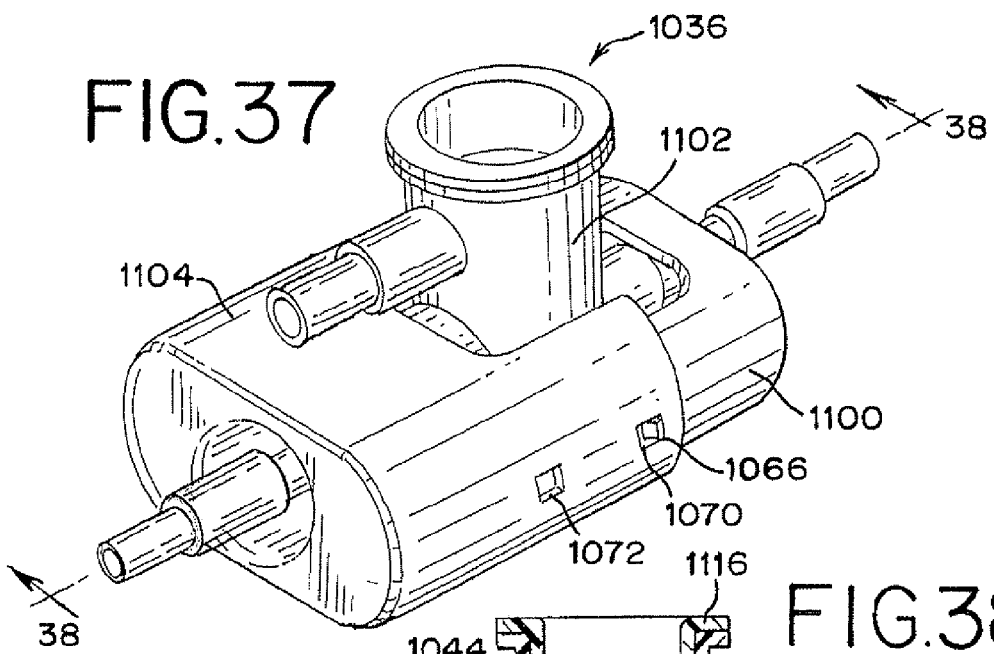
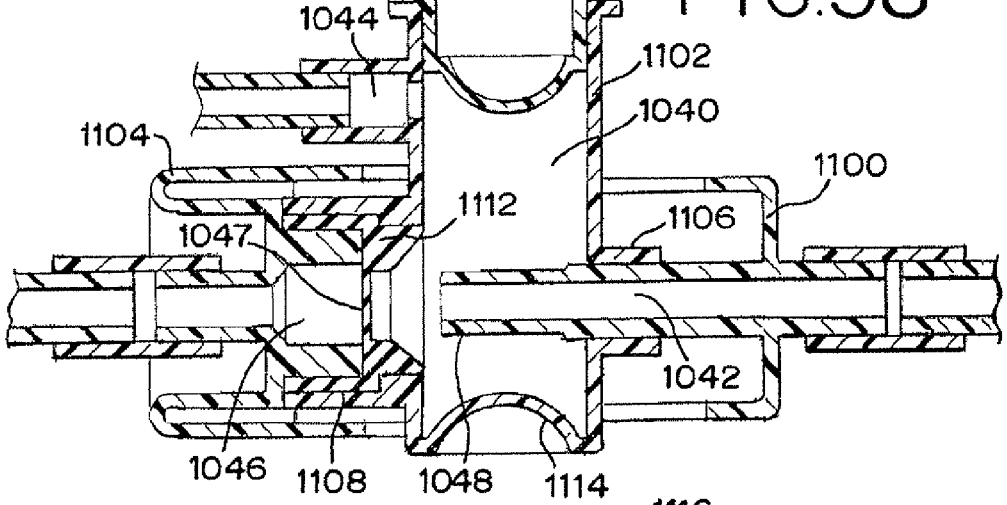
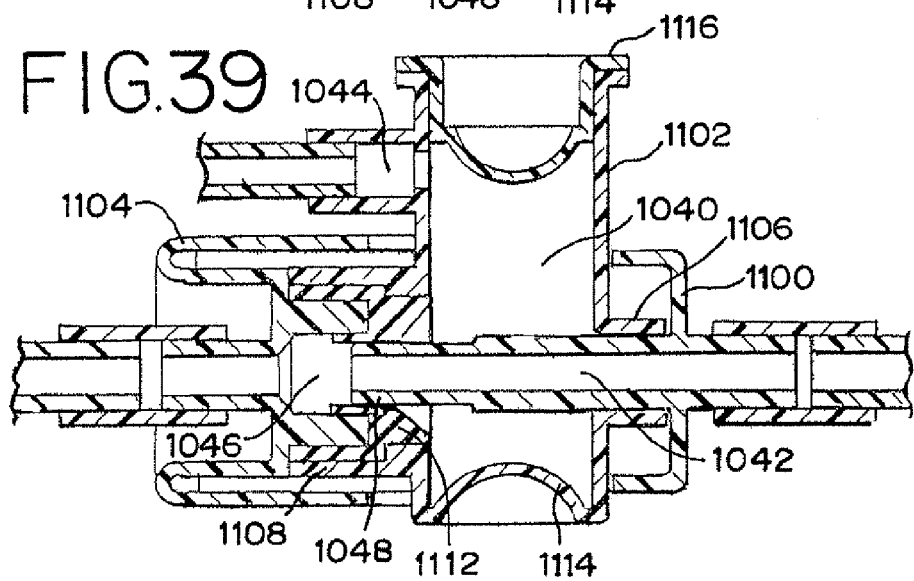

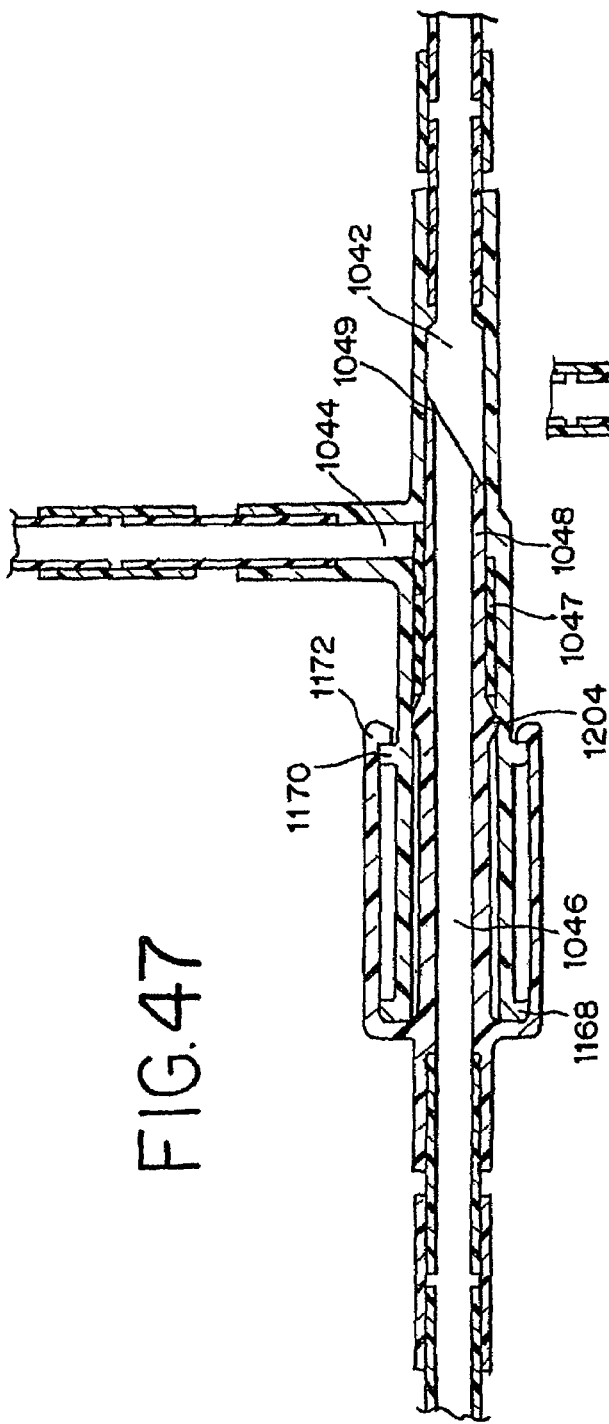
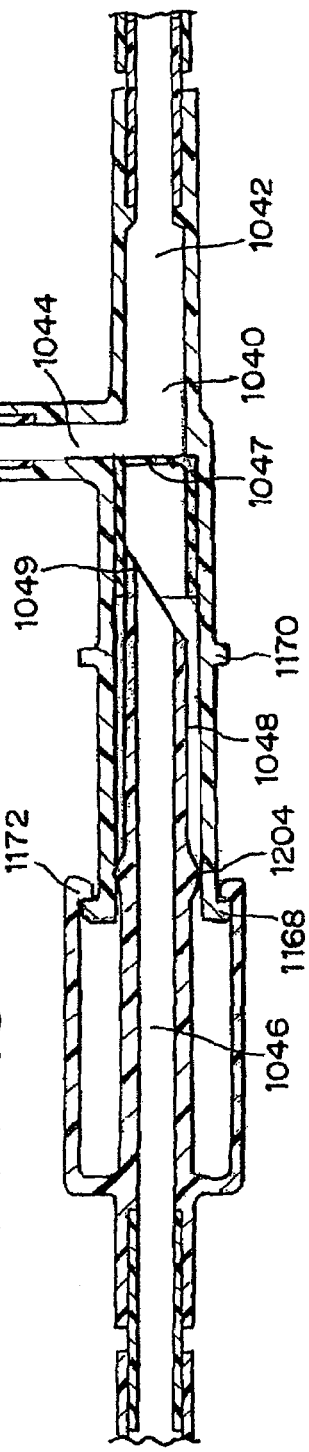
FIG. 47
FIG. 48

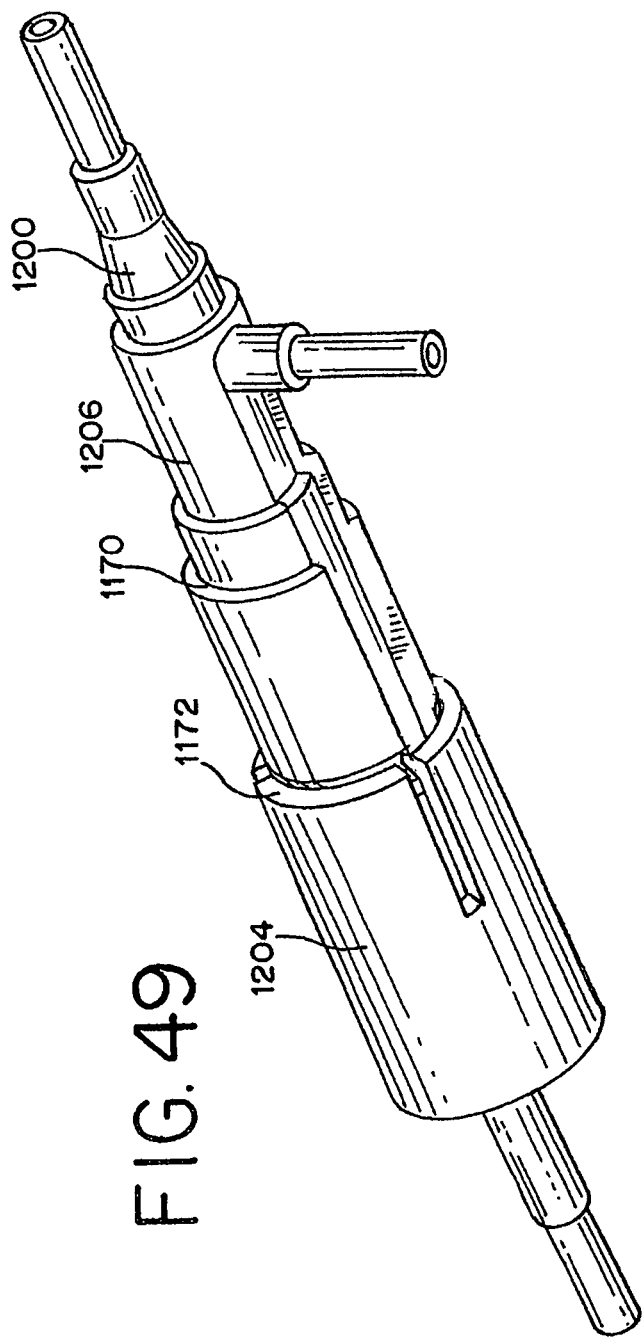

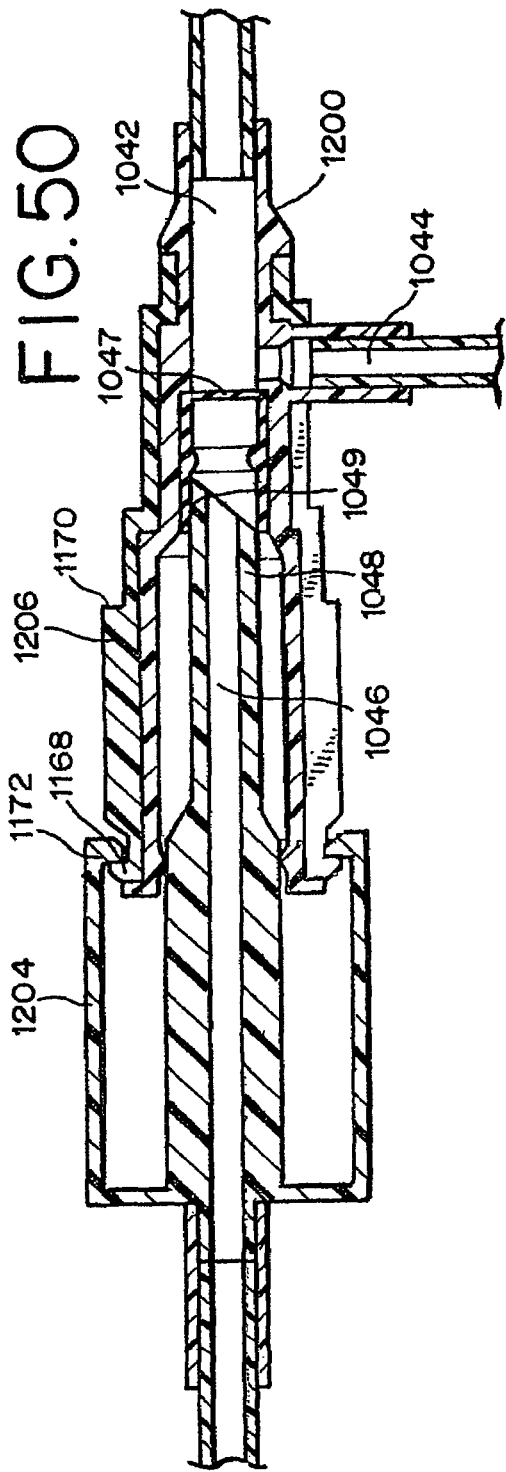
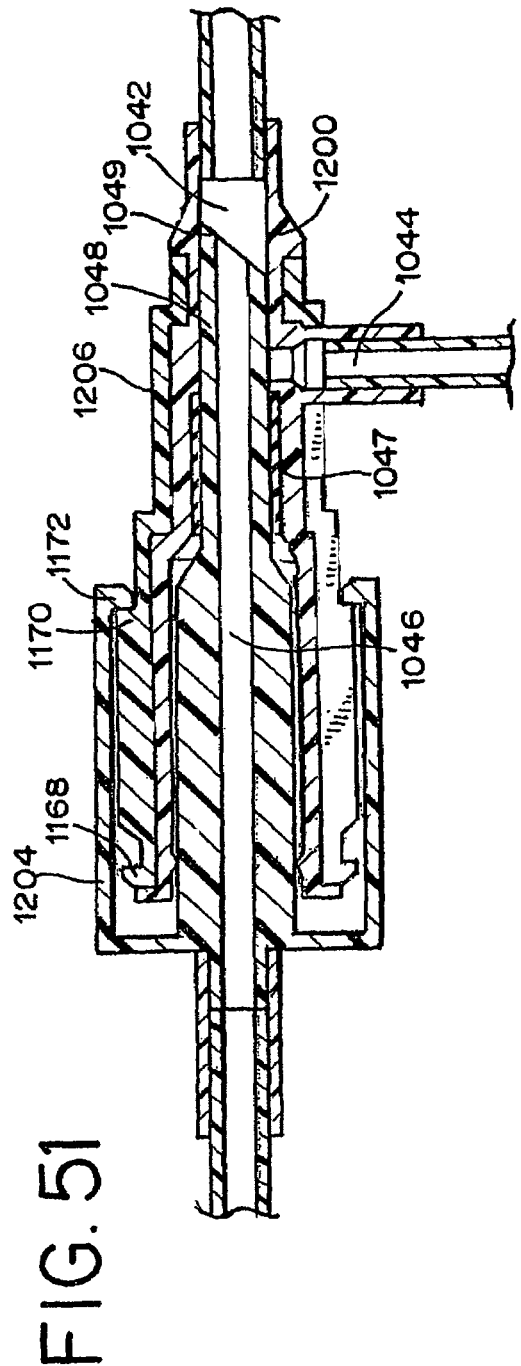

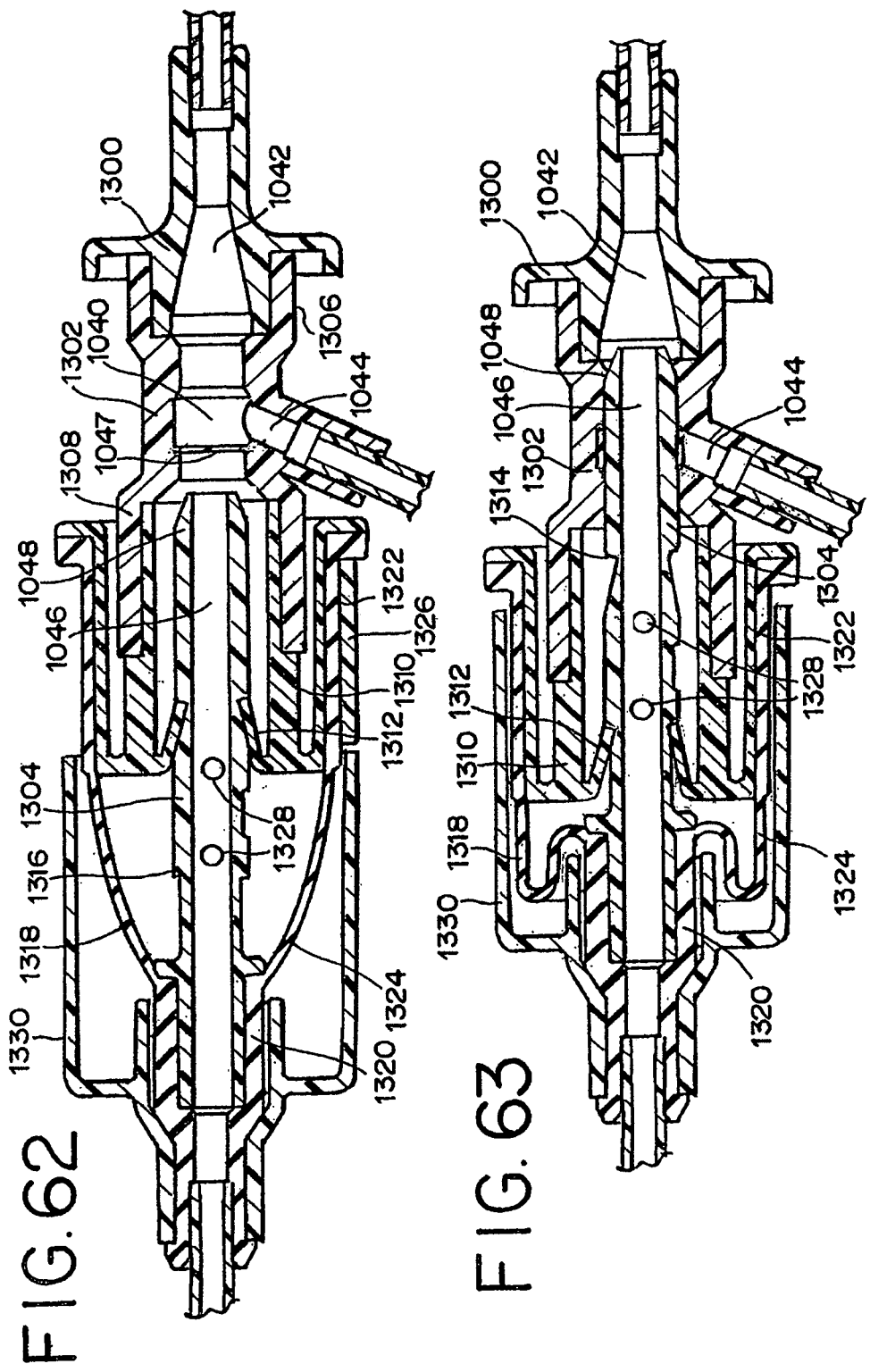

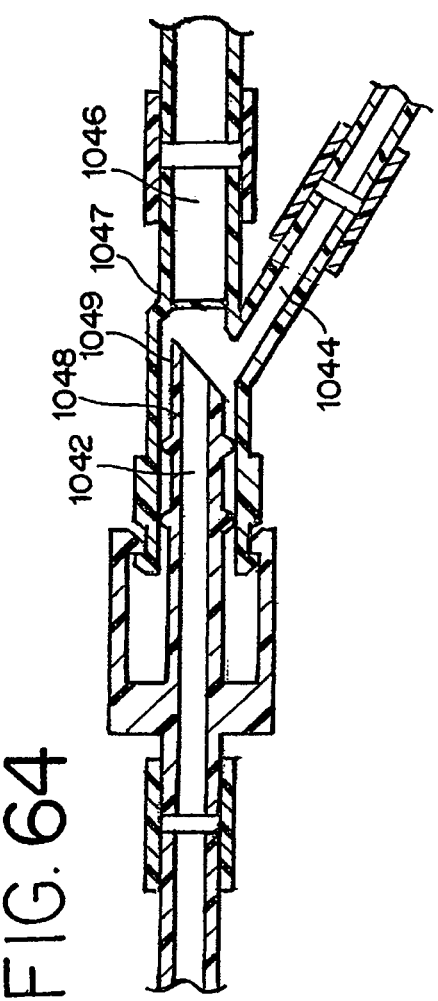
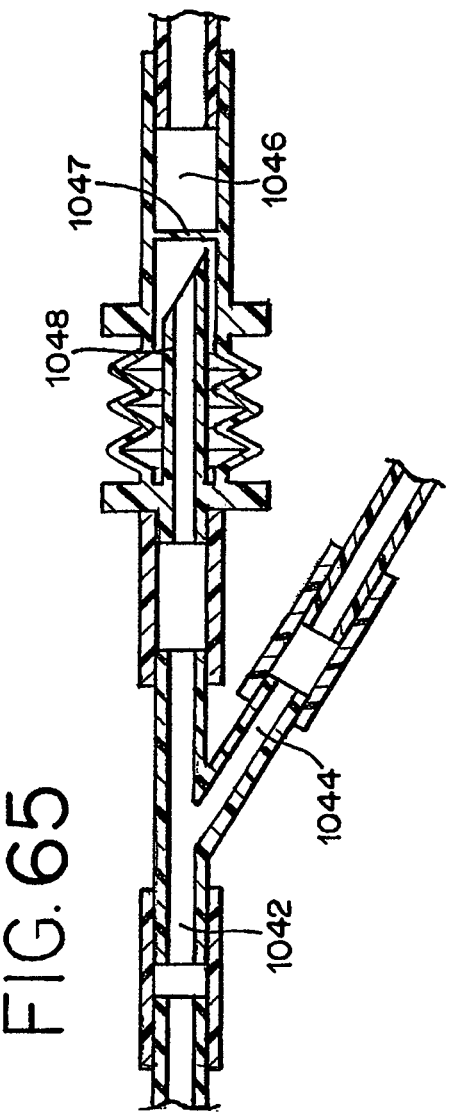
FIG. 64
FIG. 65

> US 8,443,824 B2

FLUID FLOW CONTROLLER

CROSS REFERENCE TO RELATED APPLICATION

This application claims the benefit of U.S. Provisional Application Nos. 60/978,613 filed Oct. 9, 2007; 61/031,894 filed Feb. 27, 2008; 61/031,995 filed Feb. 27, 2008; and 61/031,811 filed Feb. 27, 2008, all of which are incorporated herein by reference.

FIELD AND BACKGROUND

The present disclosure is generally directed to flow controllers that restrict, block, divert or otherwise control the flow of fluid through a liquid flow path or switch the flow of fluid between a first and second liquid flow path. More specifically, the present disclosure is directed to easy to use and ergonomical flow controllers that are more easily manipulated than current frangible sealing devices or clamps.

Fluid flow controllers are commonly used in the medical field to control fluid flow within (typically) disposable, flexible tubing and container sets used to process biological fluids (i.e., processing sets) such as, but not limited to, blood. Flow controllers may be used to initially restrict and subsequently establish fluid flow between parts of the processing set. Alternatively, flow controllers may be used to restrict or block, sometimes irreversibly, flow through an initially open flow path. In certain biological fluid processing applications, flow controllers may be used to switch (e.g., toggle) between open flow and restricted flow positions.

One of the most common types of fluid flow controllers used in the medical field is the frangible or breakable sealing device. Frangible sealing devices are often used in the medical field to initially restrict and subsequently establish fluid flow within a processing set. Current day frangible sealing devices typically include a breakable cannula within the hollow interior of a housing, disposed within the flow path of the tubing or container. The cannula blocks the flow of fluid through the hollow interior and thus prevents liquid flow through the flow path. When required, fluid flow is established by bending the housing such that the cannula within the housing breaks and ceases to block the flow of fluid within the housing and the processing set, generally. Examples of prior art frangible sealing devices (sometimes referred to herein simply as "frangibles") are provided in, for example, U.S. Pat. Nos. 4,899,903 and 5,330,464, both of which are hereby incorporated by reference in their entireties.

Current frangibles provide a one time seal in that fluid flow cannot be restricted again through the frangible once the frangible has been broken. Frangibles must be resistant to easy breakage during shipment and handling, which often means that significant force must be exerted by the user to break the frangible during use. Current day frangibles have a fairly uniform housing cross section and uniform thickness of the housing wall.

Thus, at least one of the drawbacks of current day frangibles is that they are often difficult to bend at the appropriate location and even more difficult to break. Another drawback of current day frangibles is that they do not provide adequate gripping surfaces for the user. In addition, difficult to break frangibles can also result in incomplete breakage of the internal cannula and, therefore, a less than adequately open flow path (as the broken piece may still partially occlude the fluid path, thereby restricting fluid flow). This, in turn, may result in hemolysis of the blood cells or have other deleterious effects on the blood or other biological fluid. Accordingly, there is a need for easy to use flow controllers that avoid the drawbacks of current day frangibles.

SUMMARY

In one aspect, the present disclosure is directed to a flow controller including a breakable member for restricting the flow of fluid through a flow path. The flow controller includes a housing having a longitudinal axis and an axial length with a first and second end. The housing includes a central portion and finger-gripping portions on either side of the central portion. The finger-gripping portions and central portion define an outermost surface. The outermost surface of the finger-gripping portions extend radially outwardly of the outermost surface of the central portion. The housing defines an interior flow path and includes a breakable member at least partially positioned within the interior flow path of the housing to prevent the passage of fluid through the flow path. The finger-gripping portions extend entirely around the longitudinal axis of the housing and have a cross section that is generally square-shaped with rounded corners and a concave finger-contacting surface when viewed in a plane that is perpendicular to the longitudinal axis. The housing at the central portion includes a wall having a selected thickness and the housing wall at the finger-gripping portions has a wall thickness that is greater than the wall thickness at the central portion.

In another aspect, the present disclosure is directed to a fluid flow control system. The system includes a first fluid source and a first fluid flow path in fluid communication with the first fluid source. The system includes a flow controller having a unitary housing and a longitudinal axis and an axial length with a first end and a second end. The housing includes first and second finger-gripping portions integral with a central portion that is disposed between the finger-gripping portions. The finger-gripping and central portions are defined by a continuous integrally molded housing wall. The outermost surface of the housing finger-gripping portions extend radially outwardly of the outermost surface of the central portion. The housing further defines an interior flow path for receiving a fluid flow from the first fluid flow path. The housing includes a breakable member having a stem integrally molded to a tubular member and at least partially positioned within an interior flow path of the housing to prevent the passage of fluid through the flow path. The housing wall at the central portion includes a wall having a selected thickness and the housing wall at the finger-gripping portion has a wall thickness that is greater than the wall thickness of the housing at the central portion. Each of the finger-gripping portions extends around the longitudinal axis of the housing and has a cross section that is generally square-shaped with rounded corners and a concave finger-contacting surface when viewed in a plane that is perpendicular to the longitudinal axis. The flow control system further includes a second fluid flow path in communication with the housing when the stem of the breakable member is separated from the tubular member. The system also includes a container in fluid communication with the second fluid flow path.

BRIEF DESCRIPTION OF THE FIGURES

FIG. 6 is a perspective view of an alternative embodiment of a flow controller housing.

FIG. 7 is a perspective view of another alternative embodiment of a flow controller housing.

FIG. 8 is a perspective view of another embodiment of a flow controller including a breakable (i.e., frangible) member.

FIG. 9 is a perspective view of the breakable member of the flow controller of FIG. 8.

FIG. 10 is a cross sectional view of the flow controller of FIG. 2

FIG. 11 is a perspective view of one embodiment of a flow control assembly.

FIG. 11a is a perspective view of another embodiment of a flow control assembly.

FIG. 11b is a perspective view of yet another embodiment of a flow control assembly.

FIG. 12 is a perspective view of a tube insert of a flow control assembly.

FIG. 13 is a perspective cross sectional view of the tube insert of FIG. 12;

FIG. 14 is an end view of the flow control assembly of FIG. 11.

FIG. 15 is a top view of the flow control assembly of FIG. 11.

FIG. 16 is a cross sectional view of an alternative embodiment of a tube insert of a flow control assembly.

FIG. 17 is a perspective view of another embodiment of a flow control assembly.

FIG. 18 is a front elevation view of the flow control assembly in FIG. 17 with the tube insert in the open position.

FIG. 19 is a front elevation view of the flow control assembly in FIG. 17 with the tube insert in the closed position.

FIG. 24 is a cross sectional view of yet another embodiment of a flow controller with an actuator member in the open position.

FIG. 25 is a cross sectional view of the flow controller of FIG. 24 with the actuator member in the closed position FIG. 26 is a perspective view of one embodiment of a flow controller with an access member.

FIG. 27 is a front elevational view of the flow controller of FIG. 26.

FIG. 28 is a cut away front elevational view of the flow controller of FIG. 26.

FIG. 29 is a perspective view of an access member.

FIG. 30 is a top view of the access member of FIG. 29.

FIG. 31 is a perspective view of another embodiment of a flow controller with an access member.

FIG. 37 is a perspective view of an alternative embodiment of the flow controller with an access member.

FIG. 38 is a cross sectional view of the flow controller of FIG. 35 in first position.

FIG. 39 is a cross sectional view of the flow controller of FIG. 35 in second position.

FIG. 47 is a cross sectional view of the flow controller of FIG. 46 in second position.

FIG. 48 is a cross sectional view of the flow controller of FIG. 46 in first position.

FIG. 49 is a perspective view of another embodiment of the flow controller.

FIG. 50 is a cross sectional view of the flow controller of FIG. 49 in first position.

FIG. 51 is a cross sectional view of the flow controller of FIG. 49 in second position.

FIG. 62 is a cross sectional view of the flow controller of FIG. 61 in first position.

FIG. 63 is a cross sectional view of the flow controller of FIG. 61 in second position.

FIG. 64 is a cross sectional view of an alternative embodiment of a flow controller in first position.

FIG. 65 is a cross sectional view of an additional embodiment of a flow controller in first position.

DETAILED DESCRIPTION

The flow controllers described herein may find use in any system where it is desirable or necessary to control flow through a fluid flow path. Although not limited to the medical field, flow controllers of the type described herein may be particularly useful in the medical field where disposable, plastic fluid processing sets are used for processing a biological fluid such as blood. The flow controllers described herein may be used to open an initially restricted flow path; close (reversibly or irreversibly) an initially open flow path; or switch between open flow and restricted flow positions.

The disposable blood processing set includes a venipuncture needle for insertion into the arm of the donor. The needle is attached to one end of a flexible plastic tube which provides a flow path for the blood. The flow path typically communicates with one or more plastic bags or containers for collecting the withdrawn blood.

The blood collection set may also include a sampling sub-unit. The sampling sub-unit allows for collection of a sample of blood, which sample can be used for testing of the blood (i.e., predonation). Preferably, the sample is obtained prior to the "main" collection of blood. Collecting the sample prior to the main collection reduces the risk that bacteria residing on the donors skin where the needle is inserted (i.e., in particular, the small section of detached skin commonly referred to as the "skin plug") will enter the collection container and contaminate the blood collected for transfusion. Thus, it is preferred that the blood sample, which may include the skin plug, be diverted from the main collection container. Flow controllers of the type described herein may be used to restrict, divert and/or otherwise control the flow of fluid to the sample container and the collection container.

Figure 1:
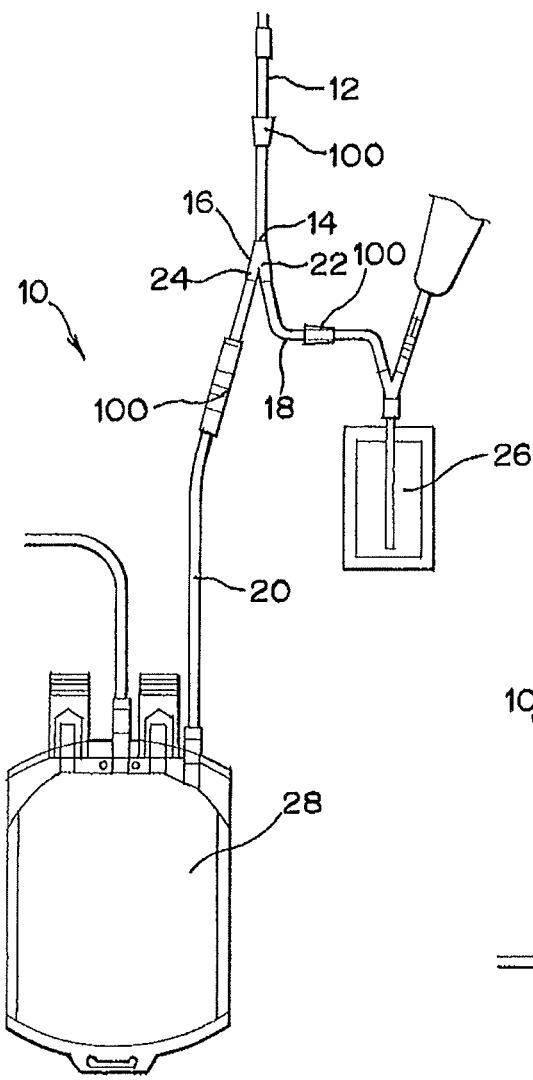
FIG. 1 is a plan view of a disposable blood processing set including flow controllers disclosed herein.

Examples of blood processing sets with such sampling sub-units are described in U.S. Pat. Nos. 6,387,086 and 6,520,948 and in U.S. Patent Application Publication Nos. 2005/0215975 and 2005/0148993. The processing sets described therein are generally illustrated in FIG. 1 at 10 and include a needle (not shown) and a length of tubing 12, defining a flow path, one end of which communicates with the needle and the other end of which communicates with the inlet port 14 of a Y-junction 16. The tubing set also includes two additional lines 18 and 20 which are branched from the outlet ports 22 and 24 of a Y-junction 16, respectively. The first branched line 18 communicates with a sample pouch 26 for collecting a smaller volume of blood from which samples may be obtained. The second branched line 20 communicates with a main collection container 28 that is typically adapted to collect a larger quantity of blood than the sample pouch 26 after the initial sample has been taken.

Figure 1A:
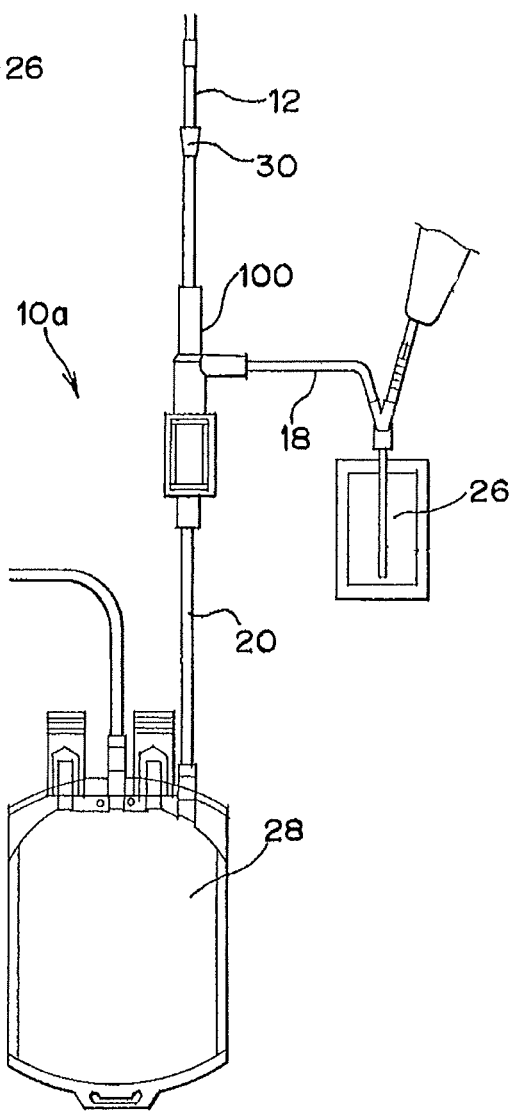
FIG. 1a is a plan view of the disposable blood processing set including another flow controller disclosed herein.

The blood collection set 10 of FIGS. 1 and 10a of FIG. 1a include flow controllers 100 for controlling the flow of biological fluid (e.g., blood) through the set. For example, the flow controllers 100 are typically placed on the tubing line 12 leading to the Y-junction 16 and on the tubing line 18 leading to the sample pouch 26, respectively. A controller 100 may also be placed on the tubing line 20 leading to the main collection container 28. By selectively opening and closing the different flow paths (by altering the flow controllers), the technician can control the flow of blood from the donor, diverting the blood to the desired output zone.

In a typical application, the flow controller 100 on the initial length of tubing 12 is closed and venipuncture is performed on the donor. Thereafter, the controllers 100 are opened to allow a small amount of blood to be collected in the sample pouch 26 for later analysis and to clear the skin plug. When the desired amount of blood has been collected in the sample pouch 26, the controller 100 between the Y-junction 16 and the sample pouch 26 is closed and the breakaway cannula 30 is broken to allow blood flow to the main collection container 28. Flow to the sample pouch 26 should be permanently closed, in order to prevent the skin plug from migrating into the main collection container 28 and to prevent anticoagulant from migrating to the sample pouch 26 from the main collection container 28. A processing set such as the one shown in FIGS. 1 and 1A may include one or more flow controllers that are non-reclosable, non-reopenable and or capable of being opened and closed As shown in FIG. 1, flow controller 100 may be located at one or more points in the processing set to restrict and, when desired, establish flow communication between different parts of the processing set or system. While the processing system described and shown in FIG. 1 is a so-called "manual" collection set, it will also be appreciated that flow controllers of the type described herein may also find application in automated systems where collection and separation occur with the donor connected to an apparatus having a disposable processing set mounted thereon. Examples of such automated systems are the Fenwal Amicus® Separator, and the Alyx® Blood Separation system, to name a few.

It will be seen from the following description that there are several possible variations and embodiments of flow controllers according to the present disclosure. Flow controllers embodying the principles described herein are simple to operate, as they may be easy to grasp and require little manipulation or force by the user. Certain embodiments of the flow controllers described herein may be actuated with one hand and involve only a button press. To further enhance safety, the flow controllers described herein may be adapted for one-time, one way operation which prevents return to from a final position to a initial position, thereby eliminating the risk of upstream or downstream contamination. However, as shown in some of the embodiments, two-way operation is also possible. In addition, some of the embodiments of the flow controllers described herein also maintain sterility of the system by providing a sanitary seal. Further details and preferred embodiments of the flow controllers are set forth below.

Flow Controller with Breakable Member

One embodiment of a flow controller described herein, generally designated as 100, is illustrated in FIGS. 2-7. The flow controller of FIGS. 2-7 is a breakable or frangible type flow control device that initially restricts flow and is manipulated (i.e., broken) by the user to establish fluid flow. The frangible flow controller 100 includes a molded housing 102 providing a hollow chamber 114 defining a flow path between an inlet 104 and outlet 106. The inlet 104 and outlet 106 may communicate with external tubing of the blood processing set (i.e. tubing line 12 see FIG. 1) that is joined to the inlet and outlet by solvent bonding or other means known to those of skill in the art.

Figure 3:
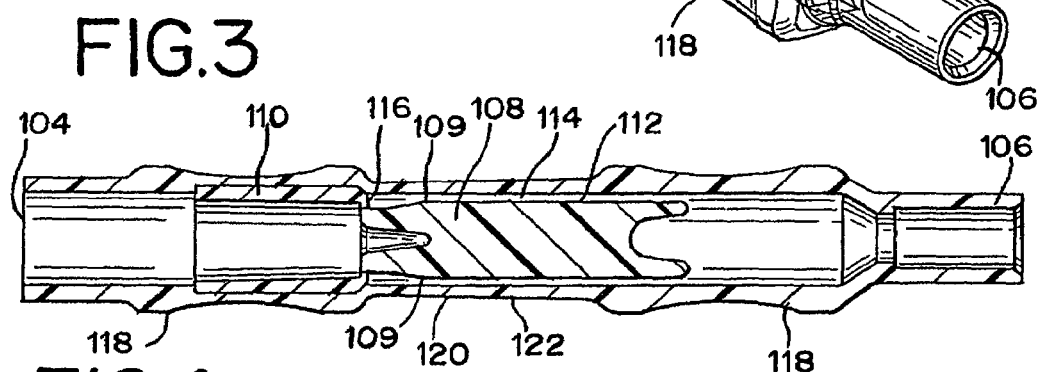
FIG. 3 is a cross sectional view of the flow controller of FIG. 2.

Within flow controller 100 and, more particularly, within hollow chamber 114 is a breakable/frangible member, generally designated at 108, which comprises a substantially tubular member 110 and an elongated, rigid member or stem 112 extending therefrom (see FIG. 3). In the initial state, the breakable member 108 is at least partially disposed within the hollow chamber 114 and blocks fluid flow between inlet 104 and outlet 106.

Figure 5:
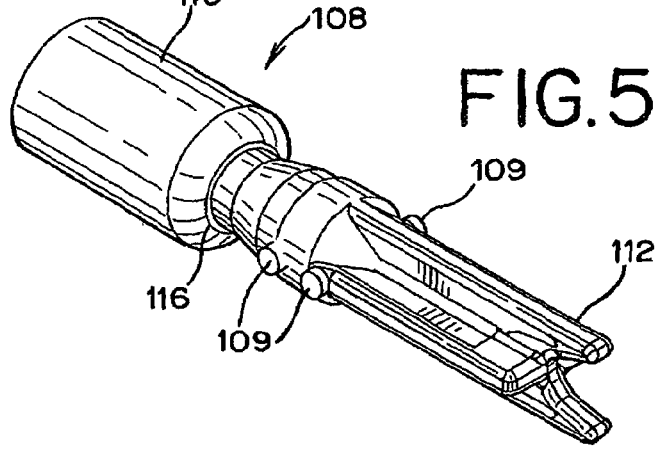
FIG. 5 perspective view of one embodiment of a breakable member of a flow controller as shown in FIG. 2.

Initially, the stem 104 of the breakable member 108 is integrally molded to interface 116 of the tubular member 110. Interface 116 has an outer diameter at least as large as the inner diameter of the flow path defined by chamber 114. Thus fluid flow cannot occur past solid interface 116. Initially, breakable member 108 occludes the opening of the tubular member 110 and prevents the flow of fluid past interface 116 and ultimately, through the flow controller 100. In one embodiment, the breakable member 108 may include optional projections 109 (see FIG. 5) that extend radially, outwardly from member 108, thereby holding breakable member 108 in place and preventing any undesired movement or shifting of member 108. Multiple projections 109 may be provided and may be aligned as opposing pairs as illustrated in FIG. 5. Alternatively, breakable member 108 may comprise a single pair of opposing projections 109.

Figure 2:
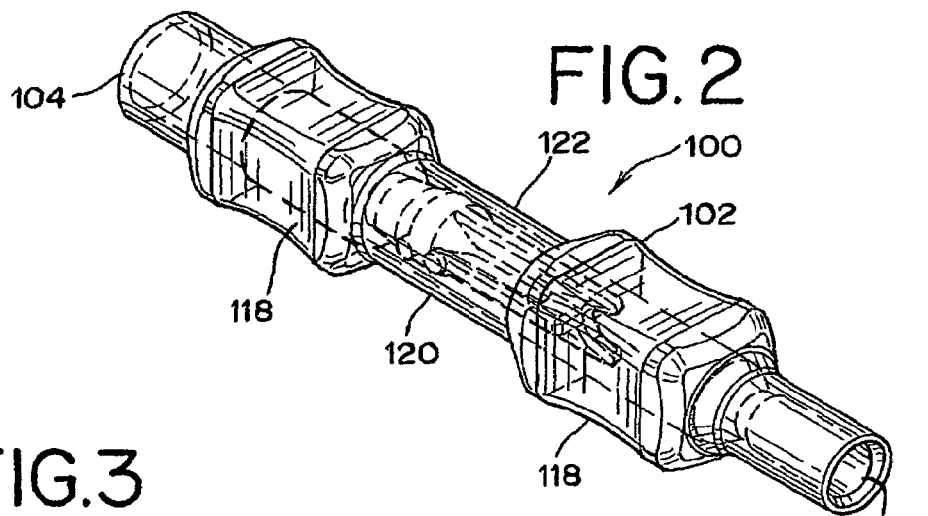
FIG. 2 is a perspective view of one embodiment of a flow controller with a breakable (i.e., frangible) member
Figure 4:
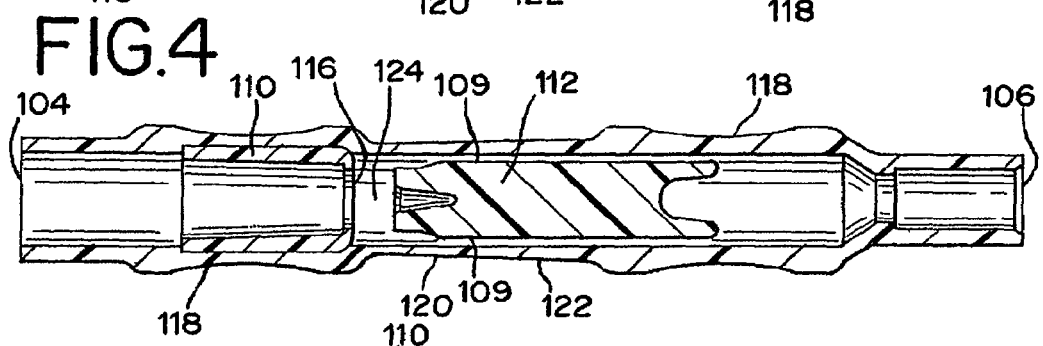
FIG. 4 is a cross sectional view of the flow controller of FIG. 2 with the breakable member broken.

As shown in FIGS. 2-4, finger-gripping portions 118 are disposed on either side of a thin walled central portion 120 of housing 102. Finger-gripping portions 118 have a cross sectional area that is greater than the cross sectional area of central portion 120 and provide sufficiently large gripping surfaces for the user to grasp when they are exerting a force to bend the molded housing 102 and ultimately break breakable member 108. Enlarged finger-gripping portions 118 are sized to reduce pressure on the user's fingers when gripped and allow for easier manipulation by the user. In addition, the thickness of the housing walls at the finger-gripping portions 118 is greater than central portion 120 (discussed in more detail below) thereby making portions 118 more rigid, sturdy and easier to firmly grasp.

Thin walled central portion 120 of housing 102 has a relatively thin wall 122 to preferably minimize the force required to cause central portion 120 of housing 102 to bend. Wall 122 of bendable central portion 120 has a thickness to allow complete collapse of breakable member 108 and thus, minimize restriction of fluid flow through the flow controller 100.

Housing 102 is preferably made of a biocompatible and heat-sterilizable material that can be bonded (by solvent bonding or other forms of sealing) to tubing such as, but not limited to polyvinyl chloride (PVC). Preferably, housing 102 is made of a substantially transparent material to allow the user to view the breakable member (and confirm that breakage has occurred). Breakable member 108 may be made of any suitable plastic material such as, but not limited to polycarbonate.

In use, the finger-gripping portions 118 are advanced towards one another and the relatively more rigid nature of finger-gripping portions 118 combined with the reduced thickness of thin exterior housing wall 122 causes molded housing 102 to bend at a point within central portion 120. Such bending force at a point in central portion 120 allows one to be able to rupture the stem 112 along interface 116. This allows the stem 112 to be separated from interface 116 of the hollow tubular member 110 and a gap 124 is created between the two portions thereby permitting flow through the flow controller 100.

As noted above, once the stem 112 is separated from tubular member 110, the optional outwardly extending projections 109 prevent any undesired movement or upward or downward tilting or shifting of separated stem 112 by maintaining the stem 112 in a relationship relative to with the inner surface of housing 102. Projections 109 may contact the outer wall of housing 10, but may also terminate just short of the housing 102 inner wall. Preferably, once separated, stem 112 can slide along the inner surface of housing 102 and stays substantially aligned with the central axis of housing 102. This orientation allows fluid to flow over and around stem 112 and fins or vanes thereon and pass through the opening in the tubular member 110.

In one embodiment, wall 122 of central portion 120 of housing 102 has a thickness that may range from about 0.005 inches to about 0.040 inches. Preferably the wall thickness of the finger-gripping portions 118 may range from about 0.040 inches to about 0.25 inches. A further discussion of the stem structure and stem breakage is provided in U.S. Pat. No. 5,330,464 which is hereby incorporated by reference in its entirety.

The finger-gripping portions 118 may have a variety of configurations. As indicated above, finger-gripping portions 118 have a cross sectional area that is greater than the central portion of housing 102. The finger-gripping portions 118 may have an exterior surface that is textured or contoured to provide ergonomic grips to ease use and comfort to the user in holding and manipulating the flow controller 100. For example, in one embodiment (shown in FIG. 2) the cross section of finger-gripping portion 118 is substantially a square with rounded corners. The surface of finger-gripping portions 118 is slightly concave to match the contour of the user's fingers. In an alternative embodiment, the finger-gripping portions 118 may have an enlarged circular configuration as shown in FIG. 6. In yet another alternative embodiment shown in FIG. 7, the finger-gripping portions 118 may include finger pads 126 that at least partially encircle housing 102. Preferably, the finger pads 126 are textured to provide gripping surfaces for the user. Finger pads 126 may be integral with housing 102 and provide a unitary molded component or, alternatively, external finger pads 126 may be separately molded components (as shown in FIG. 7) that are placed on the housing 102.

FIGS. 8-10 illustrate another embodiment of a flow controller generally designated 150. Flow controller 150 has a molded housing 152 that includes a generally hollow interior chamber. Molded housing 152 is ergonomically adapted to minimize pressure on the user's fingers when force is exerted on the molded housing 152. Molded housing 152 generally has a flattened oval cross section as seen in FIG. 10. One end of molded housing 152 narrows to an inlet 154 that may communicate with external tubing of the blood processing set (i.e. tubing line 12 see FIG. 1) that is joined to the inlet by solvent bonding or other means known to those of skill in the art.

The other end of molded housing 152 is adapted to receive insert 158 which is generally hollow. Insert 158 has an outlet 154 that may communicate with external tubing of the blood processing set (i.e. tubing line 12 see FIG. 1) that is joined to the inlet by solvent bonding or other means known to those of skill in the art. Interior interface 160 of insert 158 has a flattened oval cross section as seen in FIG. 12. A portion of insert 156 is inserted inside molded housing 152. Breakable member or stem 162 is disposed within molded housing 152 and is connected to interior interface 160. Stem 162 and interior interface 160 occludes the opening of insert 158 and prevents the flow of fluid through flow controller 150.

A portion of molded housing 152 preferably includes a thin walled central portion 164, as generally described above. Thin walled central portion 164 has a thin exterior wall 166 to minimize the force required to cause thin walled central portion 164 to bend. The point where stem 162 is connected to interior interface 160 is positioned within thin walled central portion 164 and, more specifically, where bending that portion of the housing will result in breakage (severance) of the stem from interface 160.

In the flow controller's 150 initial state, the stem 162 acts to block fluid flow through the housing 152 and between the attached tubing. When fluid flow is desired, the user grips the molded housing 152 on each side of the thin walled central portion 164 and exerts force to bend molded housing 152. The thinness of thin exterior wall 166 causes molded housing 152 to bend at a point in thin walled central portion 164. Such bending force at a point in thin walled central portion 164 causes force to be exerted on breakable member 162, thereby breaking stem 162 away from interior interface 160 and allowing fluid to flow through flow controller 150. Preferably, housing 152 of flow controller 150

Flow Control Assembly

FIGS. 11-15 illustrate an embodiment of a non-frangible flow controller 200. In this embodiment, flow controller 200 is provided as an assembly that includes a tube insert 202 and an external clamp 204. Tube insert 202 includes a tube 206 having a first end and a second end portion with a central portion therebetween. Preferably tube insert 202 and or at least central portion 210 is made of a biocompatible and flexible material that can be sterilized by autoclaving or other forms of sterilization used in the medical field. In one embodiment, at least the central portion 210 of tube 206 is comprised of a material having suitable stiffness, durometer and shape memory such that it can revert to an open position after high temperature sterilization and after remaining in a closed position for a period of several months or even years. In addition, the material of tube 206 should be such that it bonds sufficiently to external connectors 208. One such material is, for example, silicone and more particularly, silicone having a durometer of approximately 40; however, other materials known to one skilled in the art may be used.

In one embodiment, the first and second ends may likewise be made of a the material of central portion 210. In fact, entire tube insert 202 may be made of a single material (e.g., silicone or other), However, in a further embodiment first and second end portions may include two or more materials. For example, in one embodiment, first and second end portions may be provided with an outer sleeve or layer over the tube insert 206. In one embodiment, connectors 208 may be made of any material that is bondable to tube 206; however, in an alternative embodiment the connectors 208 may be constructed integrally with tube 206. In a preferred embodiment, the connectors 208 may be constructed of polycarbonate; however, other suitable materials that are compatible for bonding or joining to tubing of the fluid processing set (i.e. tubing line 12 see FIG. 1) may be used.

Tube insert 202 is seated within external clamp body 204. External clamp body 204 defines a U-shaped channel 214 in which tube insert 202 is seated. First wall 216 of U-shaped channel 214 defines a cutout 218 that extends completely through the first wall 216 of U-shaped channel 214. Second wall 222 contains cutout 224 on inside portion of second wall 222. Plunger 220 is slidably positioned through cutouts 216 and 214.

In use, plunger 220 interacts with the "exposed" bendable central portion 210 of tube 206 between first and second ends. In the closed position, plunger 220 occludes fluid flow through tube 206 by compressing the central portion 210 against the U-shaped channel 214. The locking plunger can be advanced further through cutouts 216 and 214 such that central portion 210 is not compressed and fluid is able to flow through tube 206.

Plunger 220 includes a blade portion 226 extending from a handle portion 228. In the illustrated embodiment, the blade portion 226 is generally rectangular and has a first portion 230 and second portion 232. The first portion 230 of blade portion 226 is configured such that when first portion 230 is positioned within the U-shaped cannel 214 fluid is occluded from flowing through tube 206. The second portion 232 of blade portion 226 defines a cutout configured such that when the second portion 232 is positioned within the U-shaped channel 214 of clamp 204 fluid is able to flow through tube 206. Preferably, the cutout is an arc and more preferably, the arc has at least the same diameter as central portion 210 of tube 206. It is understood, that the first portion 230 and second portion 232 can be switched such that when the plunger is in the first position fluid is able to flow through the flow control assembly.

The handle portion 228 may be sized to provide a gripping surface for the user to manipulate the plunger 222. In addition, the handle portion 228 may be oversized to help prevent the plunger 222 from passing through cutout 218 in the first wall 216 of the external clamp 204.

FIG. 16 illustrates another embodiment of a tube insert 240 that can be used with the external clamp 204 previously discussed. In this embodiment, tube insert 240 is provided as an outer housing 242 molded around tube 244. Preferably the outer housing 242 is of a material adapted for bonding or joinder with the material of the tubing of the processing set, such as polyvinyl chloride (PVC). Tube 244 may preferably be made of a silicone as describe above; however, other materials could be used and would be known to those of skill in the art. The outer housing 242 substantially completely encapsulates tube 244 to, for example, prevent leakage. The walls of housing 242 surrounding the central portion of tube 244 are sufficiently thin such that the once clamp 204 is opened after being closed for an extended period of time (such as even several years), the walls of housing 242 open back up to allow fluid flow through the tube insert 240.

Tube 244 is preferably constructed of a material having a suitable stiffness and durometer of about 80 such that tube 244 is capable of forcing open the thin walls of housing 242 once the clamp 204 is opened or removed. Both ends 246 of tube insert 240 are adapted to connect to external tubing (i.e. tubing line 12 see FIG. 1). As mentioned above, tube insert 240 may likewise be seated within external clamp body 204.

Alternate embodiments of clamps 204 suitable for use with tubes of the above described embodiments are shown in FIGS. 11a and 11b. For example, FIG. 11a illustrates an embodiment of clamp 204 wherein two interlocking arms 234 are pressed together to pinch together central section 210 of tube 206 and occlude flow. Arms 234 may be released from one another to open the flow path. FIG. 11b illustrates another embodiment of a clamp 204, wherein flow may be established by sliding clamp 204 over tube insert 206. Clamp 204 has a cover portion 236 that has a member that interacts with central section 210 of tube 206. These clamps may be irreversibly closed or both openable and closeable.

FIGS. 17-19 illustrate another embodiment of a nonfrangible flow controller generally designated 250. In this embodiment, flow controller assembly 250 includes the tube insert 202 as previously described above and an external clamp 254. Alternatively, tube insert 240 or any other suitable tube known to those of skill in the art could be used instead of tube insert 202. Tube insert 202 is seated within an external clamp body 254. The clamp body 254 includes a base 256 with a first arm 258 and a second arm 260 extending from the base.

The clamp body 254 defines a channel 262 between arms 258, 260 in which tube insert 202 is slidably positioned. Channel 262 includes a flow portion 264 and an occlusion portion 266. The flow portion 264 is sized to allow the flexible central portion 210 of tube insert 202 to remain in at least a partially non-compressed position, thereby allowing fluid flow through the tube. Occlusion portion 266 of channel 262 is sufficiently sized to compress central portion 210 of tube insert 202 to restrict fluid flow. Therefore, when no fluid flow is desired, the tube is moved through the channel 262 from the flow portion 264 to the occlusion portion 266 of channel 262 and vice versa when flow is desired.

At least one of the first arm 258 or second arm 260 is slightly resilient. The arms 258, 260 may bend or flex outwardly to accommodate the movement of the tube through the channel 262, yet will return to the original configuration once the tube has passed through the channel 262 due to the resiliency. However, arms 258, 260 must have enough resistance against flexing outwardly such that it would take a significantly larger force than normally encountered in the ordinary use of the clamp 254 to move the tube through channel 262. In one embodiment, at least one of the arms 258, 260 may include a rib 268. Rib 268 may be sized to provide additional stiffness to external clamp body 254. Rib 268 may also be sized to provide a guiding edge for external connectors 208 of tube insert 202.

Within the channel 262, at least one of the arms 258, 260 may preferably include ramp 270. Ramp 270 helps guide the tube insert 202 as it is moved from the flow portion 264 to the occlusion portion 266 of channel 262. Ramp 270 also provides a detent action against allowing tube insert 202 to easily move from flow portion 264 to the occlusion portion 266. In the embodiment shown in FIGS. 17-19, the ramp provides a rounded taper in both directions of the channel 262; i.e., towards the occlusion portion 266 and towards the flow portion 264. The ramp 270 is therefore bilateral, or two-way, in that a tube 202 can be moved from either the occlusion portion 266 into the flow portion 264 or vice versa. However, ramp 270 may also tapered in one direction only allowing the tube to be moved through the channel 262 in one direction. Because of the particular configuration of the arms 258, 260 and ramp 270, the clamp 254 has a spring-like characteristic. Thus, when adequate force from the tube 202 is applied to the arms 258, 260, the arms 258, 260 flex away from the tube 202 permitting the tube to pass over the ramp 270 and into the selected portions of the channel 262.

In one embodiment, tube insert 202 is inserted into channel 262 through opening 272. At least one of the arms 258, 260 has a beam 274 that is at least partially disposed within opening 272 and thus functions as a guide that directs tube insert 202 into the channel 262 and functions as a stop that resists movement of a tube that has been placed in the channel 262 from easily being removed from the clamp 254. Beam 274 is at least slightly resilient wherein it can flex inwards when tube insert 202 is inserted and deflect outward to prevent the easy removal of a tube from the clamp 254.

Flow Controller with Actuator Member

FIGS. 20-25 illustrate embodiments of flow controllers 300 having a body or housing 302 adapted to receive an actuator member 308. The actuator member 308 is adapted for movement within the housing 302 to selectively bring the fluid inlet 304 into flow communication with the fluid outlet 306. The actuator 308 is adapted for at least substantially non-rotational movement and more preferably no rotational movement between first and second positions. As used herein "substantially non-rotational" means no more than de minimus movement of the actuator about a central axis. "Substantially non-rotational" movement falls short of a rotational movement that would allow an inlet to be in flow communication with an outlet.

Figure 20:
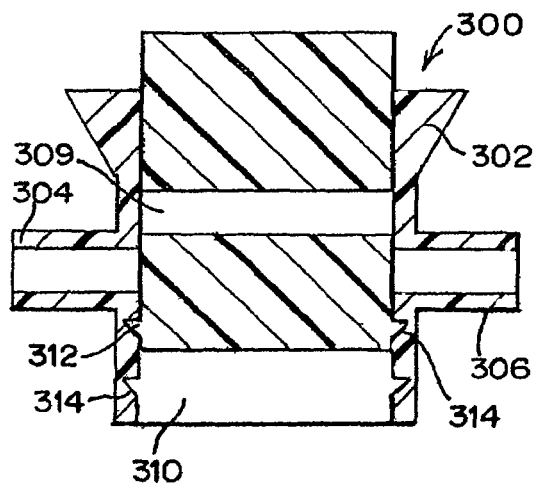
FIG. 20 is a cross sectional view of one embodiment of a flow controller with an actuator member in the closed position.
Figure 21:
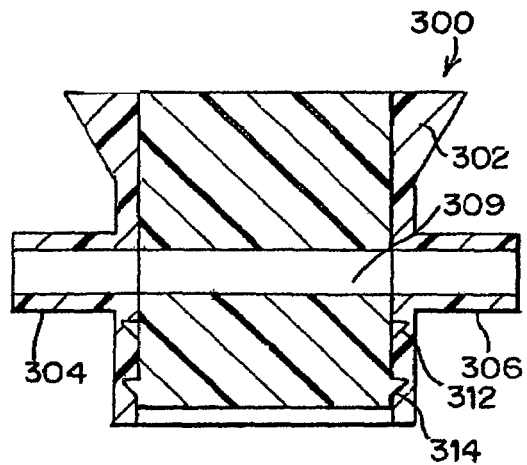
FIG. 21 is a cross sectional view of the flow controller of FIG. 20 with the actuator member in the open position.
Figure 22:
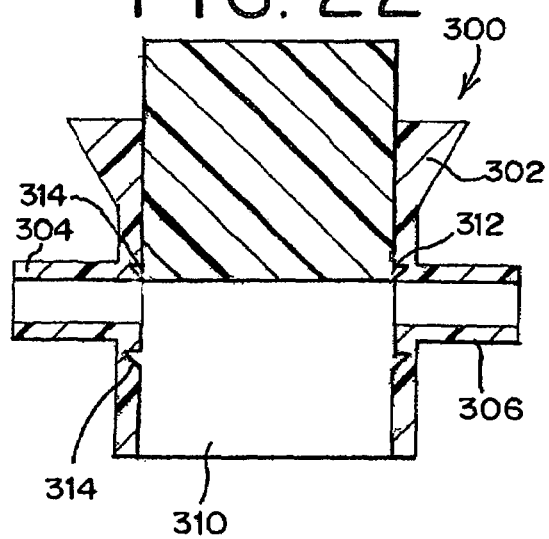
FIG. 22 is a cross sectional view of another embodiment of a flow controller with an actuator member in the open position.
Figure 23:
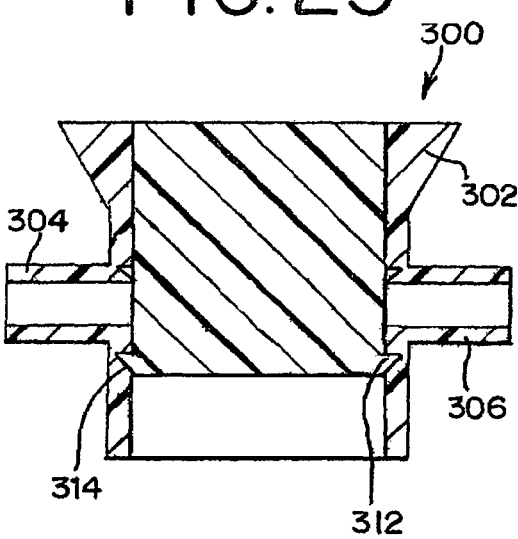
FIG. 23 is a cross sectional view of the flow controller of FIG. 22 with the actuator member in the closed position.

As best illustrated in FIG. 20, the housing 302 defines an open-top cavity 310 in communication with the fluid inlet 304 and fluid outlet 306 through sidewalls. The cavity 310 is adapted to receive the actuator member or button 308, also illustrated in FIG. 20. The actuator member 308 is preferably initially provided in a first position, which can either result in a closed flow controller (FIGS. 20 and 21) or open flow controller (see FIGS. 22 and 23).

In one embodiment, the actuator member 308 is a solid member that preferably defines a flow path or channel 309 that extends throughout the actuator member 308. In order to establish fluid flow through the flow controller 300, channel 309 is aligned with the fluid inlet 304 and fluid outlet 306. In an alternative embodiment illustrated in FIGS. 22 and 23, the actuator member is a solid member, for example, a plug or a stop.

To move from the first position to the second position and ultimately initiate or restrict fluid flow between the fluid inlet 304 and the fluid outlet 306 of the housing 302, the actuator member 308 is advanced further into the housing cavity 310, or downwardly in terms of the orientation of FIGS. 20-23. To maintain the actuator member 308 in the second position, the flow controller 300 may include a lock mechanism. The lock mechanism may consist of interacting apertures and tabs, latch arms and grooves or any other suitable locking mechanism. In the illustrated embodiment, the locking mechanism generally includes latches 312 (shown in FIGS. 20-23) provided on the actuator member 308. The latches 312 have a flat, outwardly extending top surface that interacts with corresponding grooves 314 defined in the cavity 310 like a ratchet pawl to prevent return movement from the second position to the first position. In one embodiment, the cavity 310 may have a set of grooves in which the latches may be seated in when the actuator member 308 is in the first position. The configuration of latches 312 and grooves 314 is such that the actuator member 308 can be advanced from the first position to the second position.

To prevent the actuator member 308 from moving past or overshooting the second position, it may be provided with an oversized endcap that contacts and interferes with the seat of the body cavity 310 to prevent further advancement of the actuator member 308 into the cavity 310. Alternatively or additionally, the bottom surface of the actuator member 308 may be adapted to contact the bottom surface of the cavity 310 in the second position to prevent further advancement of the actuator member 308 into the cavity 310.

An additional embodiment of a flow controller flow controllers 300 having an actuator member 308 is shown in FIGS. 24 and 25. The flow controller of FIGS. 24-25 is similar to the flow controller of FIGS. 20-23 and similar or identical elements will be referred to with identical reference numerals. In this embodiment the actuator member 308 is movable in two (opposite) directions with a depressible button associated with each end of actuator 308.

The actuator member is a solid member that preferably defines a flow path or channel 309 that extends throughout the actuator member 308. In order to establish fluid flow through the flow controller 300, channel 309 is aligned with the fluid inlet 304 and fluid outlet 306. In this embodiment, the positioning of the actuator member 308 may be reversible.

The actuator member 308 may be comprised of any of a number of materials. For example, in one embodiment, the actuator member 308 is relatively rigid or non-compressible, and comprised of a material such as polypropylene. It may be preferred to use a rigid actuator member, because such a member provides a more secure fit with the cavity grooves and an improved tactile and/or audible indication when moved to the second position. In particular, the latch of the locking mechanism may make a "clicking" noise when it snaps into place in the groove of the housing 302. This is merely one possible indicating means and those of ordinary skill in the art will recognize that others are available and may be practiced with this aspect of the present disclosed subject matter.

Alternatively, the actuator member 308 may be comprised of a less rigid, more deformable material. A more deformable actuator member is less dependent on precise manufacturing tolerances than a more rigid one, and may be better suited to providing a leak-resistant fit against the body cavity. On the other hand, the actuator member 308 should not be overly deformable, otherwise it will deform when pressed, instead of moving to the second position. Further, a latch made of an overly deformable material may be insufficient to lock into a groove to prevent movement from the second position to the first position. It has been found that an actuator member 308 having a Shore hardness rating of approximately 80 will function properly, without suffering from any of the above drawbacks. In particular, suitable materials include Cawiton SEBS, manufactured by Wittenburg B.V. of Hoevelaken, Netherlands, and Santoprene® thermoplastic elastomer, manufactured by Advanced Elastomer Systems, LP of Akron, Ohio. These materials are especially suitable for use with a relatively rigid body formed of polycarbonate, because they will not become bonded thereto if the flow controller 300 is subjected to a steam sterilization process at approximately 240° F.

Contamination of the fluid, especially if the fluid is blood, should be prevented, so the body 302 may be provided with a sanitary seal or membrane bonded to the surface that covers the cavity and encloses the actuator member 308. Preferably, the membrane is sufficiently deformable to flex and allow the actuator member 308 to be moved from the first position to the second position. To ensure that membrane does not become overly taut when actuator member 308 is depressed, the membrane may be provided with excess material. Polyvinyl chloride (PVC) is a suitable material for the membrane and may be RF heat-sealed to the body 302, but other materials may be used without departing from the scope of the present invention.

To further promote a sanitary collection environment, the flow controller itself may be sterilized prior to use. Preferably, the body 302 and actuator member 308 are irradiated and steam sterilized during manufacture to ensure that the flow controller 300 and associated tubing and containers are sterile. One possible problem with steam sterilization, which may be carried out at approximately 240° F., is that the heat may tend to cause the body to deform, thereby degrading performance. For example, in one embodiment, the body is formed of PVC, which is useful for bonding to PVC tubing and a PVC sealing membrane, but can shrink and deform during steam sterilization.

Flow controllers illustrated in FIGS. 20-25 are similar to in many respects to flow controllers described in U.S. patent application Ser. Nos. 11/555,797 and 11/555,868 filed on Nov. 2, 2006 both assigned to the assignee of the present application and hereby incorporated by reference in their entireties. The materials and components described therein may also have application to the flow controllers of the present disclosure. Whereas the flow controllers described in the above-referenced applications in large part describe flow diversion from one flow path to another flow path, the flow controller described herein provides an on-off switch for fluid flow generally.

Flow Controller with an Access Member

FIGS. 26-69 illustrate additional embodiments of flow controllers having an access member to establish fluid flow therethrough and within a fluid processing set.

One embodiment of such a flow controller is illustrated in FIGS. 26-28. As shown in FIG. 26, flow controller 400 has a housing 402 with a hollow interior defining a flow path that communicates with fluid ports 404 and 406 (see FIG. 28). Housing 402 is preferably made of a biocompatible and heat-sterilizable material that can be bonded (by solvent bonding or other forms of flow control) to tubing such as, but not limited to polyvinyl chloride (PVC).

In one embodiment, housing 402 is made by mating housing subassembly 408 and housing subassembly 410. Housing subassembly 408 and housing subassembly 410 are sealed together at center 412 to form housing 402 by an appropriate sealing technology, for example, RF welding. As illustrated in FIG. 28, housing subassembly 408 defines sub chamber 414, port 404 and flow channel 416. Housing subassembly 410 defines sub chamber 418, port 406 and flow channel 420. Ports 404 and 406 are the fluid inlet and fluid outlet of the housing 402. Sub chamber 414 and sub chamber 418 together form chamber 422 which can accommodate a small volume of a liquid. As shown in FIG. 28, sub chambers 414 and 418 are defined by thin pliable wall 424 of their respective housing subassemblies.

The wall thickness of the housing subassemblies should be such that the sub chambers defined thereby can collapse towards center 412 (see FIG. 28) when pressure is exerted inwardly on housing 402 by the user. More particularly, the thickness of thin pliable wall 424 should be such to minimize the force required to collapse sub chambers 414, 420. In one embodiment, thin pliable wall 424 has a typical thickness that may range from about 0.010 inches to about 0.030 inches. Thin pliable wall 424 may be transparent to allow visibility inside chamber 422.

Ports 404 and 406 are adapted to receive and convey respectively, a fluid therethrough. As shown in FIG. 28, tubing may be joined to ports 404 and 406. Tubing is joined to ports 404 and 406 by conventional means such as solvent bonding. Ports 404 and 406 are defined by wall 426 that is preferably more rigid than thin pliable wall 424 to thereby allow ports 404 and 406 to reasonably maintain their shape when pressure is exerted on housing 402 to cause sub chambers 414, 418 to collapse toward center 412. In one embodiment, the wall thickness of wall 426 of ports 404 and 406 has a typical thickness of about 0.030 inches to about 0.060 inches. The exterior of ports 404 and 406 may provide gripping structure such as ridges or roughened surfaces to aid the user in handling of the flow controller. Additionally, wall 426 may be transparent to allow visibility inside ports 404 and 406.

Disposed within housing subassembly 408 of flow controller 400, and more particularly the internal flow channel 416, is sealing member 428 (FIG. 28). In a preferred embodiment, sealing member 428 may be a plug, cap, membrane or other structure that occludes the flow path, but is engageable and accessible by an access member 430. In one embodiment, sealing member 428 is a membrane made of a biocompatible material such as plastic, silicone or other material. As shown in FIG. 25, sealing member 428 is disposed across flow channel 416 in housing subassembly 408 such that fluid flow through housing assembly 408 is prevented until sealing member 428 is accessed.

Disposed within housing subassembly 410 and (partially) extending into housing subassembly 408 is access member 430. Access member 430 is shown in more detail in FIGS. 29 and 30. In one embodiment, access member 430 may be an integral part of housing subassembly 410. For example, access member 430 may be an engaging end of flow channel 420. Alternatively, access member 430 may be a separate component that is bonded to housing subassembly 410. Access member 430 may have a hollow interior in flow communication with flow channel 420. As shown in FIG. 28, tip 432 of access member 430 is proximate to sealing member 428 and may be provided in the shape of a piercing spike. Access member 430 contains at least one opening 434 (FIG. 29) through which fluid can flow. Access member 430 is constructed of a material that is more rigid than the material of membrane 428.

In use, a portion of access member 430, including tip 432, penetrates sealing member 428 when sufficient compressive force is exerted on housing subassemblies 408 and 410 towards center 412. After penetration of sealing member 428, access member 430 is held in place by a retention means such as a friction fit with flow channel 416 or a one way snap element (not shown).

With reference to FIG. 28, in its initial state, flow controller 400, and more specifically, sealing member 428 acts to block fluid flow between the attached tubing. When fluid flow is desired, the user grips ports 404 and 406 of flow controller 400 and exerts force towards center 412. The relatively more rigid nature of ports 404 and 406, combined with the reduced thickness of thin pliable wall 424, causes sub chambers 414 and 418 to collapse toward center 412. Such collapsing force causes access member 430 to move toward and penetrate sealing member 428, thus allowing fluid to flow through the flow path of the flow controller 400.

Figure 32:
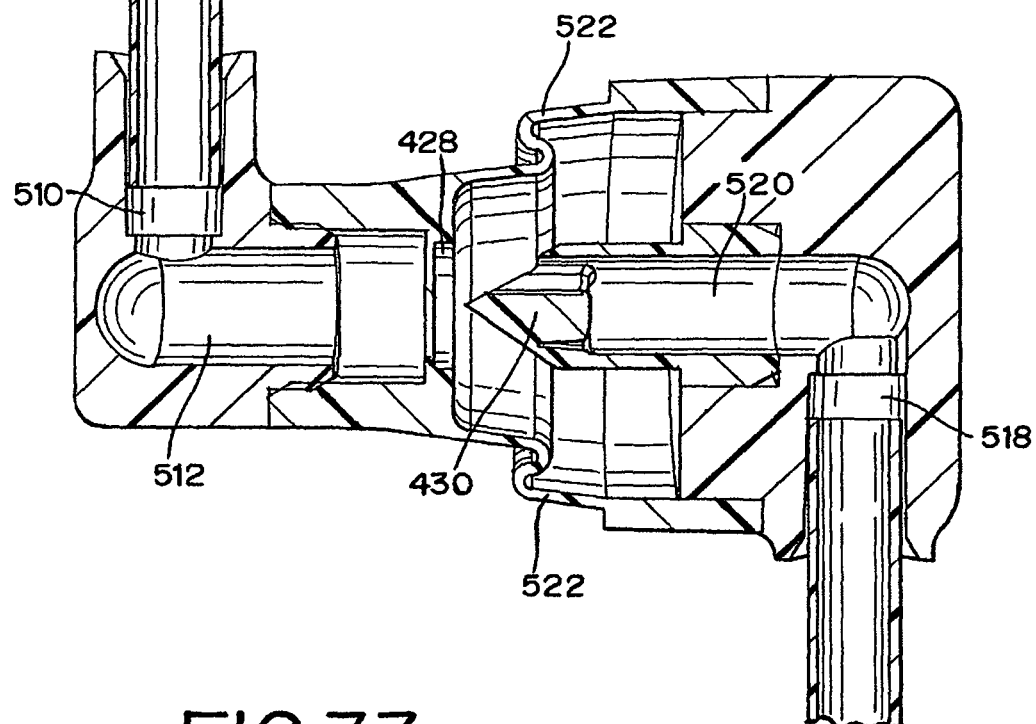
FIG. 32 is a cut away top view of the flow controller of FIG. 31.
Figure 33:
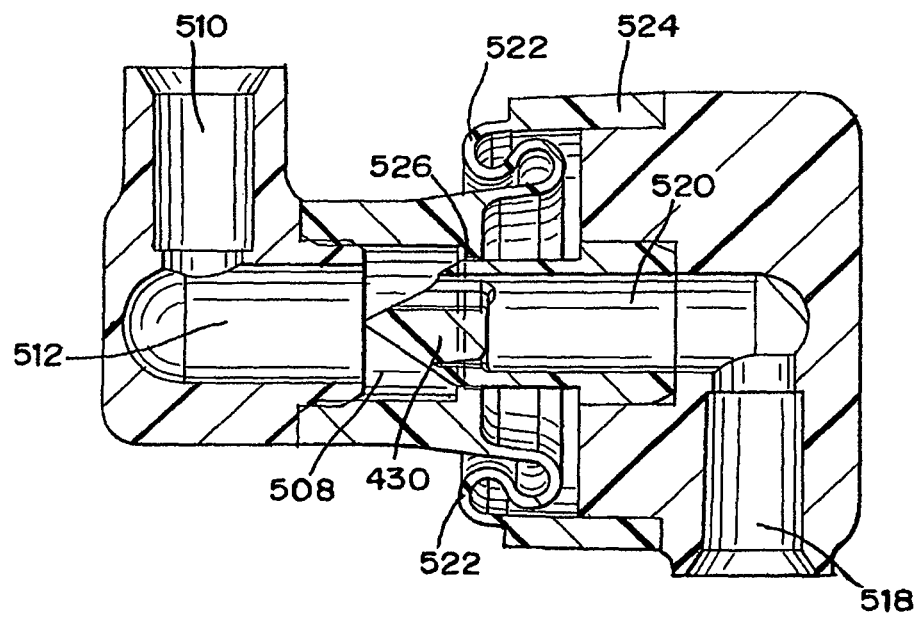
FIG. 33 is a cut away top view of the flow controller of FIG. 31 in a compressed state.

FIGS. 31-33 illustrate another embodiment of a flow controller generally designated 500. Flow controller 500 has a central housing 502 having a generally hollow interior. End 504 of central housing 502 is connected to end cap 506. End 504 defines flow channel 508. End cap 506 includes access port 510 and interior flow channel 512. End 514 of central housing 502 is connected to end cap 516. End cap 516 includes access port 518 and flow channel 520.

Central housing 502 is preferably made of a biocompatible and heat-sterilizable material that can be bonded to end cap 506 and end cap 516. End cap 506 and end cap 516 are preferably made of a biocompatible and heat-sterilizable material that can be bonded (by solvent bonding or other forms of flow control) to tubing such as, but not limited to, polyvinyl chloride (PVC). The outer surfaces of end cap 506 and end cap 516 may contain gripping surfaces provided by ridges or a roughened surface. As in the flow controller of FIGS. 26-28, central housing 502 is defined by thin pliable wall 522 that collapses inwardly when pressure is exerted inward on end cap 506 and end cap 516. The thickness of thin pliable wall 522 is such to minimize the force required to collapse end 504 and end 514 of central housing 502. In one embodiment, thin pliable wall 522 has a typical thickness of 0.010 inches to 0.030 inches. Thin pliable wall 522 may be transparent to allow visibility inside central housing 502.

Ports 510 and 518 are adapted to receive and convey a liquid therethrough. Tubing may be joined to access ports 510 and 518. Ports 510 and 518 may communicate with external tubing of the blood processing set (i.e. tubing line 12 see FIG. 1) that is joined to the ports by solvent bonding or other means known to those of skill in the art. End cap 506 and end cap 516 are defined by wall 524 that is preferably more rigid than thin pliable wall 522 to thereby allow end cap 506 and end cap 516 to reasonably maintain their shape when pressure is exerted on central housing 502 to cause end 504 and end 514 to collapse inwardly. In one embodiment, the wall thickness of wall 524 of end cap 506 and end cap 516 has a typical thickness of 0.030 inches to 0.060 inches. Wall 524 may be transparent to allow visibility inside end cap 506 and end cap 516.

Disposed within central housing 502 of flow controller 500 is a sealing member such as, but not limited to, membrane 526 (FIG. 32). In one embodiment, membrane 526 is made of a biocompatible material such as plastic, silicone or other material. As shown in FIG. 32, membrane 526 is disposed across flow channel 508 in end 504 such that fluid flow through housing assembly 502 is prevented until membrane 526 is accessed (FIG. 33).

Disposed within central housing 502 is access member 430. Access member 430 is shown in more detail in FIGS. 29-30. As described in connection with the embodiment of FIGS. 26-28, access member 430 may be an integral part of flow controller 500 and more particularly of end cap 516. Alternatively, access member 430 may be a separate component that is bonded to end cap 516. Access member 430 may have a hollow interior and the base of access member 430 is in flow communication with flow channel 520. The tip 432 of access member 430 is proximate to membrane 526 and may be provided in the shape of a piercing spike. Access member 430 contains at least one opening 434 (FIG. 30) such that fluid can flow through. Access member 430 is constructed of a material that is more rigid than the material of membrane 526. In use, a portion of access member 430, including tip 432, penetrates access site (i.e. membrane 526) when sufficient force is exerted on end cap 506 and end cap 516. After penetration of membrane 526, access member 430 is held in place by a retention means such as a friction fit with housing flow channel 508 or a one way snap element (not shown).

In its initial state, flow controller 500, and more specifically, membrane 526 acts to block fluid flow between the attached tubing. When fluid flow is desired, the user grips end cap 506 and end cap 516 of flow controller 500 and exerts force inwardly. The relatively more rigid nature of end cap 506 and end cap 516, combined with the reduced thickness of thin pliable wall 522, causes end 504 and end 514 to collapse inwardly. Such collapsing force causes access member 430 to penetrate membrane 526, thus allowing fluid to flow through flow controller 500.

Figure 34:
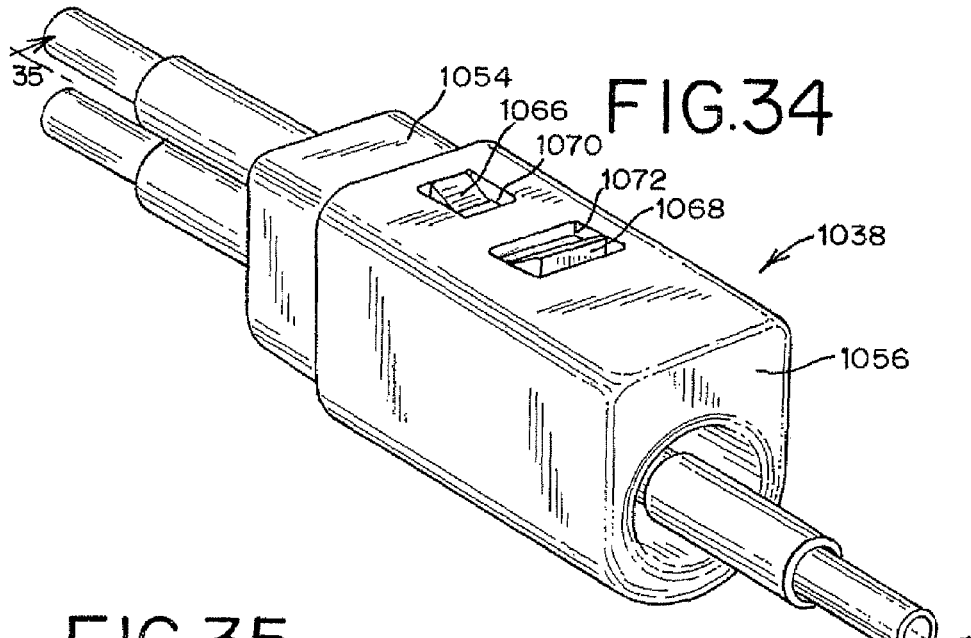
FIG. 34 is a perspective view of yet another embodiment of the flow controller with an access member.
Figure 35:
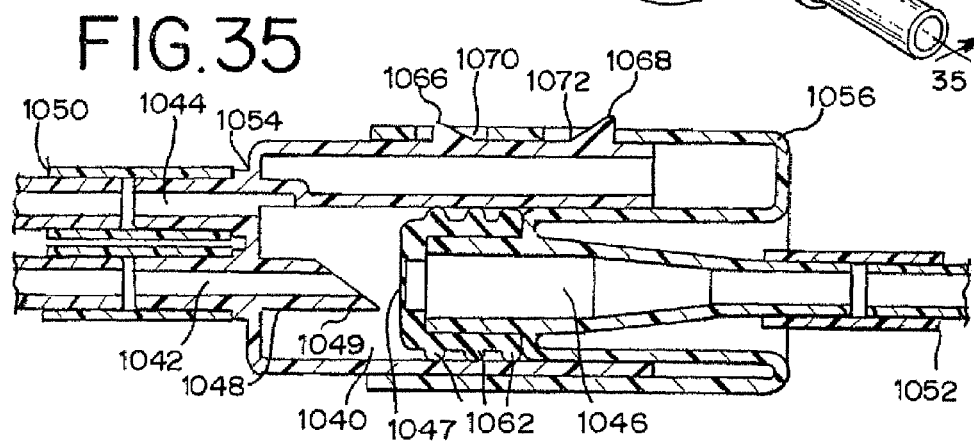
FIG. 35 is a cross sectional view of the flow controller of FIG. 34 in first position.
Figure 36:
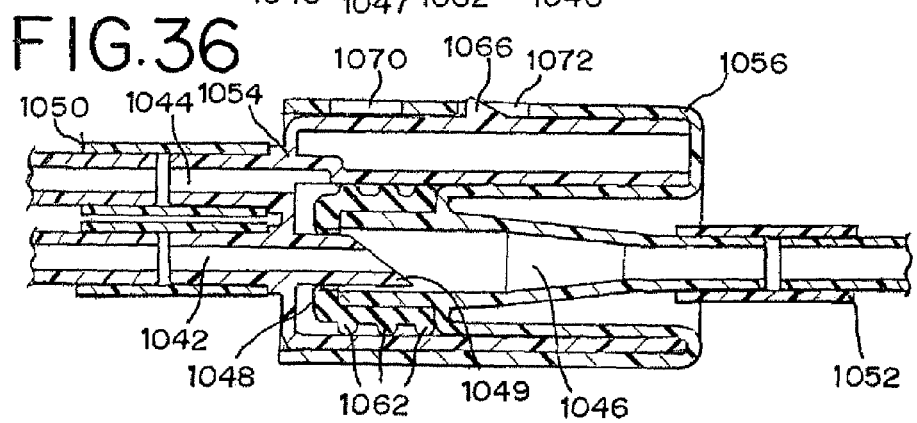
FIG. 36 is a cross sectional view of the flow controller of FIG. 34 in second position.

Other embodiments of flow controller 100 are illustrated in FIGS. 34-65. These flow controllers have an inlet and can selectively switch or direct fluid flow through one of two outlets. Therefore, they can be used as shown in FIG. 1a. Another embodiment of the flow controller is illustrated in FIGS. 34-36. The flow controller 1036 includes a housing assembly 1036 which defines a chamber 1040 therein. The housing assembly 1036 is typically comprised of a sterilized plastic material such as polyvinyl chloride (PVC), polycarbonate or some combination of the two materials. In addition, other materials may be used without departing from the scope of the present disclosure. In one embodiment the housing assembly 1038 includes an inlet 1042, a first outlet 1044, and a second outlet 1046. The end 1050 of the first outlet 1044 and the end 1052 of the second outlet 1046 are in fluid communication with the chamber 1040.

The inlet 1042 and the outlets 1044, 1046 are preferably adapted for connection with flexible tubing according to known construction. The inlet 1042 is in flow communication with a fluid source, such as a donor, typically by a venous access device such as phlebotomy needle, while the outlets 1044, 1046 are communicable with separate collection zones, preferably a sample pouch and a main collection container. Inlet 1042 and the outlets 1044, 1046 are preferably coaxial and have minimal fluid flow resistance to avoid hemolysis, clotting and "quantity not sufficient" collections.

As shown in FIG. 35, the housing assembly 1038 includes a first housing subassembly 1054 slidably disposed in a second housing subassembly 1056. The fitting of the housing subassemblies provides for a relatively tight and secure fit in order to prevent fluid leakage from the chamber 1040. As shown in FIG. 36, the first housing subassembly 1054 carries the inlet 1042 and first outlet 1044, while the second housing subassembly 1056 carries the second outlet 1046. The first housing subassembly 1054 has the inlet 1042 and first outlet 1044 aligned in a substantially parallel orientation but a number of other orientations are possible. Of course, the interfitment of the housing subassemblies may be reversed with the second housing subassembly 1056 disposed in the first housing subassembly 1054 (not illustrated).

The flow controller also includes an access member 1048 for establishing flow communication between the inlet 1042 and second outlet 1046. In one embodiment the access member 1048 may be part of the inlet 1042. In another embodiment, the access member 1048 may be part of the second outlet 1046. The access member 1048 may be in the form of a hollow channel, cannula, needle and is adapted to engage the sealing member 1047 which is described in more detail below. Alternatively or additionally, the end of the access member 1048 may define a piercing end 1049 to help pierce a sealing member 1047. The piercing end may be a sharp point or an oblique angle or bevel adapted to pierce through the sealing member 1047.

In order to prevent fluid from flowing into the second outlet 1046, a sealing member 1047 is provided in the housing assembly to isolate the second outlet 1046 from the chamber 1040 until flow through the second outlet 1046 is desired. In addition, the sealing member 1047 prevents migration of anticoagulant fluid from the collection container into the sample container. The sealing member 1047, preferably in the form of a pierceable membrane, is positioned in front of the second outlet 1046 to hermetically seal the second outlet 1046. The sealing member 1047 may be bonded (i.e., heat sealed) and integrally molded to the housing assembly or the sealing member may be a separate molded component that is positioned in the housing assembly 1038. The sealing member 1047 may be made of polyvinyl chloride (PVC), silicone or any other relatively compliant and biocompatible material that can adjust to varying pressures in the chamber 1040. Other materials may be used without departing from the scope of the present disclosure. The sealing member 1047 may take such forms as a single membrane or a hollow tube with an end closed by a membrane; however, other forms may be suitable to prevent fluid flow into the second outlet 1046.

As seen in FIGS. 34 and 35 the housing assembly 1038 of the flow controller is preferably initially provided in a first position wherein the first housing subassembly 1054 is partially disposed within the second housing subassembly 1056 at a point before the access member 1048 engages the sealing member 1047. Preferably, the access member 1048 is initially positioned very close to the sealing member 1047. This reduces the stroke length or distance the access member 1048 defined on the inlet 1042 or outlet 1046 must travel to engage the sealing member 1047 in the second position. As shown in FIG. 35, in this first position, fluid flows into the chamber 1040 through the inlet 1042 and exits the chamber 1040 through the first outlet 1044. The sealing member 1047 prevents fluid from flowing into the second outlet 1046.

To initiate fluid flow through the second outlet 1046, the housing assembly 1038 can be placed into a second position. This position is illustrated in FIG. 36, wherein the second outlet is linearly advanced further into first housing subassembly 1054. Advancing the second outlet 1046 rather than the access member 1048 prevents a pulling force on the tubing leading to the donor. In this position, fluid flow is established between the inlet 1042 and the second outlet 1046 by the access member 1048 engaging (e.g., by piercing) the sealing member 1047 and entering the second outlet 1046. The end of the access member 1048 experiences a friction fit as it engages second outlet 1046. The inlet 1042 and the second outlet 1046 are aligned along a longitudinal axis in their respective housing subassemblies such that they can engage in this manner. In this configuration, fluid only flows from the inlet 1042 through the second outlet 1046. As illustrated in FIG. 36, fluid flow through the first outlet 1044 is prevented in the second position.

Regardless of the position, the housing assembly 1038 is hermetically sealed. The hermetic seal must also be maintained during movement between positions. In the first position, there is typically an interference fit between the first and second housing subassemblies 1054, 1056, while in the second position, there may typically be an additional interference fit between the access member 1048 and the second outlet 1046. Other ways of hermetically sealing the housing assembly 1038 may be used and are more fully discussed below. Flanges, sealing surfaces, bellows assemblies, or any other suitable member may be provided in order to help maintain the hermetic seal. For example, the sealing member 1047 may include at least one sealing ring 1062 mounted on its exterior. The sealing ring 1062 interacts with the first housing subassembly 1054 to maintain a hermetic seal.

To maintain the housing assembly 1038 in the first and/or second positions, the housing assembly 1038 is preferably provided with a lock mechanism. The lock mechanism may consist of interacting apertures and tabs, latch arms and grooves or any other suitable locking means. In one embodiment, the locking mechanism generally includes at least two apertures and a corresponding tab associated with the first and second housing subassemblies. Preferably, the second housing subassembly 1056 includes, for example, two apertures 1070, 1072 that receive two tabs 1066, 1068 located on the first housing subassembly 1054 to lock the housing assembly 1038 in a position. When the housing assembly 1038 is in the first position, the apertures 1070, 1072 receive tabs 1066, 1068 respectively. Preferably, the structure of tab 1068 prevents it from interacting with aperture 1070. For example, tab 1068 may be too wide to fit into aperture 1070.

In order to adapt the housing assembly 1038 to the second position, tab 1068 is depressed and the first housing subassembly 1054 can be further advanced into the second housing subassembly 1056 until aperture 1072 receives tab 1066 which likewise results in access member 1048 engaging sealing member 1047. Of course if the second housing subassembly 1056 is advanceable in the first housing subassembly 1054, the placement of the tabs and apertures may be reversed, with the apertures on the first housing subassembly 1054 and the tabs on the second housing subassembly 1056 (not shown). In any event, the locking mechanism prevents movement from the second position back to the first FIGS. 37-39 disclose another embodiment of the flow controller and is likewise generally referred to by the reference numeral 1036. The flow controller of FIGS. 37-39 is similar to the flow controller of FIGS. 34-36 and similar or identical elements will be referred to with identical reference numerals.

In this embodiment, the housing assembly 1038 includes three housing subassemblies. As seen in FIGS. 37 and 39, the first housing subassembly 1100 carries the inlet 1042. The second housing subassembly 1102 defines a chamber 1040 and carries the first outlet 1044, inlet port 1106 and second outlet port 1108. The third housing subassembly 1104 carries the second outlet 1046.

The three subassemblies are assembled together such that the inlet 1042 of the first housing subassembly 1100 is inserted into the chamber 1040 through the inlet port 1106 of the second housing subassembly 1102 and the second outlet 1046 of the third housing subassembly 1104 is inserted into the second housing subassembly 1102 through the second outlet port 1108. In order to maintain a hermetic seal, an interference fit between the inlet 1042 and second outlet 1046 and their respective ports is established.

As shown in FIG. 39, the second housing subassembly 1102 defines a chamber 1040 and a flow path for fluid from the inlet 1042 to flow to the first outlet 1044. The chamber 1040 is sealed by a bottom closure 1114 and a top closure 1116. In one embodiment, the top closure 1116 may typically be a cap that is hermetically sealed to the second housing assembly. The bottom closure 1114 and top closure 1116 preferably are shaped with a curve inwards towards the chamber. The flexibility of the cap may accommodate pressure changes in the chamber 1040.

In this embodiment, the access member 1048 is preferably provided as part of the first housing subassembly 1100 and more specifically the inlet 1042. Preferably, the access member 1048, as illustrated in FIG. 38 is in the form of a hollow channel. In this embodiment, the sealing member 1047 is a hollow tube mounted on the end of the second outlet as best seen in FIG. 38. The tube has one end closed by a membrane that prevents fluid from flowing into the second outlet until desired. The end of the tube with the membrane is positioned closest to the first outlet 1044.

As previously described, the housing assembly is initially provided in a first position and can be adapted to a second position. In the first position, the access member 1048 is preferably positioned close to the sealing member 1047 but does not engage it. In this position fluid flows into the chamber 1040 through the inlet 1042 and flows out of the chamber through the first outlet 1044 (and to, for example, sample pouch 1026). The sealing member 1047 prevents fluid from flowing into the second outlet 1046 until desired.

To initiate fluid flow through the second outlet 1046, the first housing subassembly 1100 is advanced towards the third housing subassembly 1104. In this position, fluid flow is established between the inlet 1042 and the second outlet 1046 by the access member 1048 engaging (e.g., by piercing) the sealing member 1047 and entering the second outlet 1046. Preferably, the sealing member 1047 includes a guide member 1112 that helps direct the access member 1048 into the second outlet 1046. The end of the access member 1048 establishes a friction fit as it engages the second outlet 1046. The inlet 1042 and the second outlet 1046 are aligned along a longitudinal axis in their respective housing subassemblies such that they can engage in this manner. In this configuration, fluid only flows from the inlet 1042 through the second outlet 1046. As illustrated in FIG. 39, fluid flow through the first outlet 1044 is prevented in the second position.

To maintain the housing assembly in the first and second positions, the housing assembly is preferably provided with a lock mechanism. In this embodiment, the locking mechanism generally includes at least two apertures and a corresponding tab. Preferably, the third housing subassembly 1104 has two apertures 1070, 1072 that can interact with tab 1066 located on the first housing subassembly 1102 to lock the housing in a position. When the housing assembly 1038 is in the first position, aperture 1070 receives tab 1066.

In order to place the housing assembly 1038 in the second position, tab 1066 is depressed and the housing assembly 1036 can be adapted to where aperture 1072 receives tab 1066. Of course the placement of the tabs and apertures may be reversed, with the apertures on the first housing subassembly 1100 and the tab on the third housing subassembly 1104 (not shown).

Figure 40:
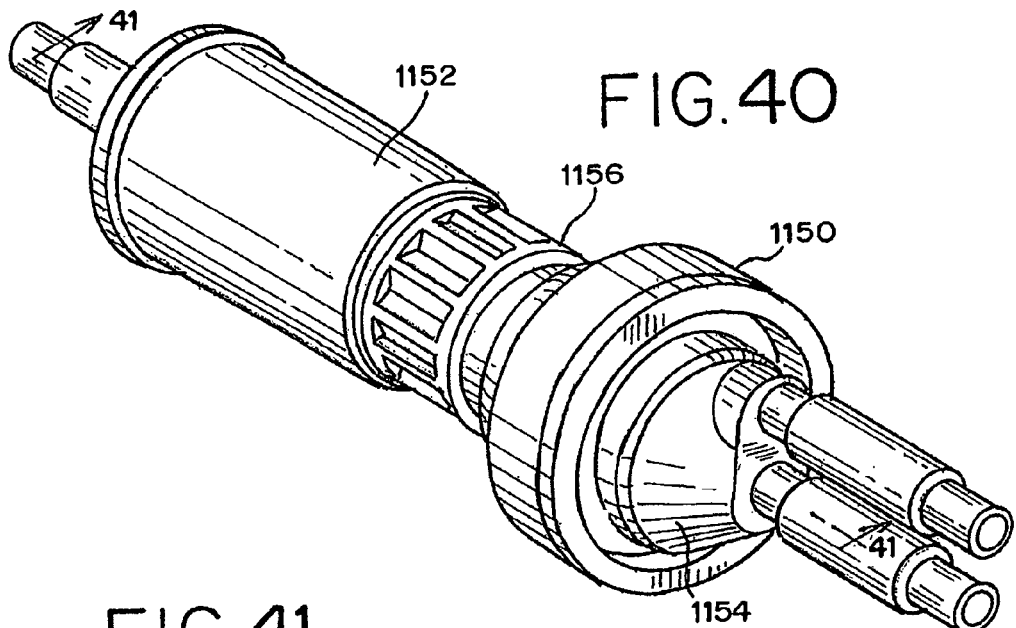
FIG. 40 is a perspective view of yet another alternative embodiment of the flow controller with an access member.
Figure 41:
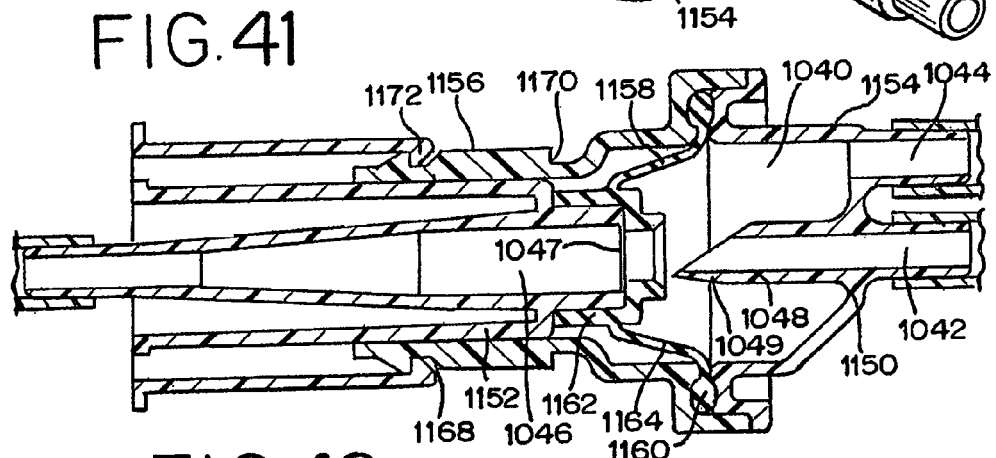
FIG. 41 is a cross sectional view of the flow controller of FIG. 40 in first position.
Figure 42:
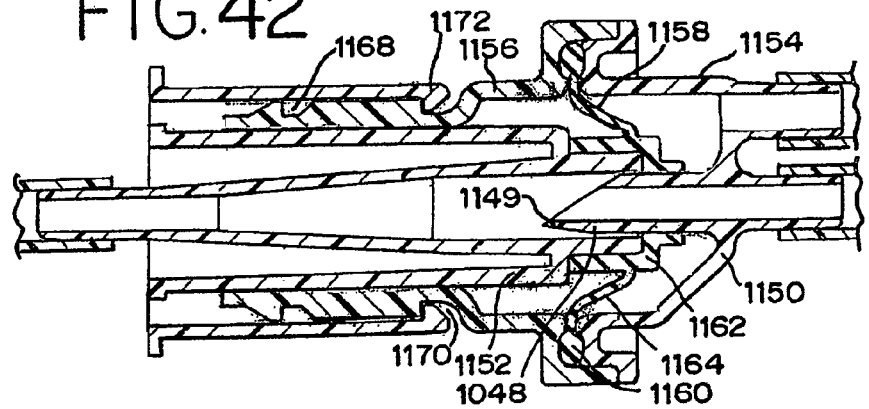
FIG. 42 is a cross sectional view of the flow controller of FIG. 40 in second position.

FIGS. 40-42 illustrate another alternative embodiment of the flow controller. The flow controller of FIGS. 40-42 is similar to the flow controllers of FIGS. 34-39 and similar or identical elements will be referred to with identical reference numerals.

As shown in FIGS. 40-42, the housing assembly 1038 includes a first housing subassembly 1150 and a second housing subassembly 1152. The first housing subassembly 1150 includes a body 1154 and an extension 1156. The body 1154 of the first housing subassembly 1150 carries the inlet 1042 and first outlet 1044. In this embodiment, the access member 1048 is defined on the end of inlet 1042 and is a hollow channel preferably provided with a piercing end 1049.

The second housing subassembly 1152 carries the second outlet 1048. A sealing member 1047 blocks the end 1052 of the second outlet 1046 to prevent fluid from flowing from the chamber 1040 into the second outlet. In this embodiment, the sealing member 1047 is a membrane mounted on or preferably joined to the end of the second outlet 1046 to prevent fluid flow therein.

Figure 43:
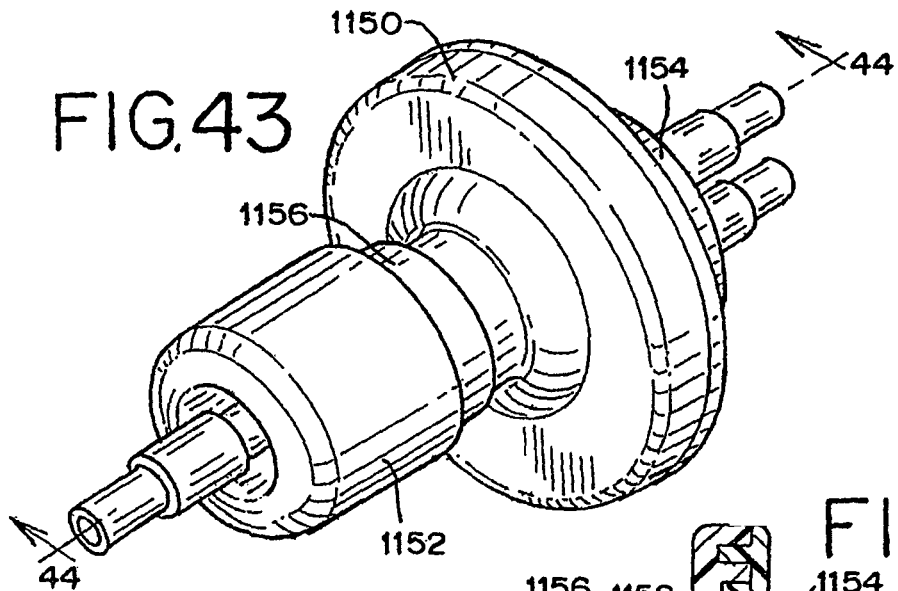
FIG. 43 is a perspective view of the yet another embodiment of the flow controller.
Figure 44:
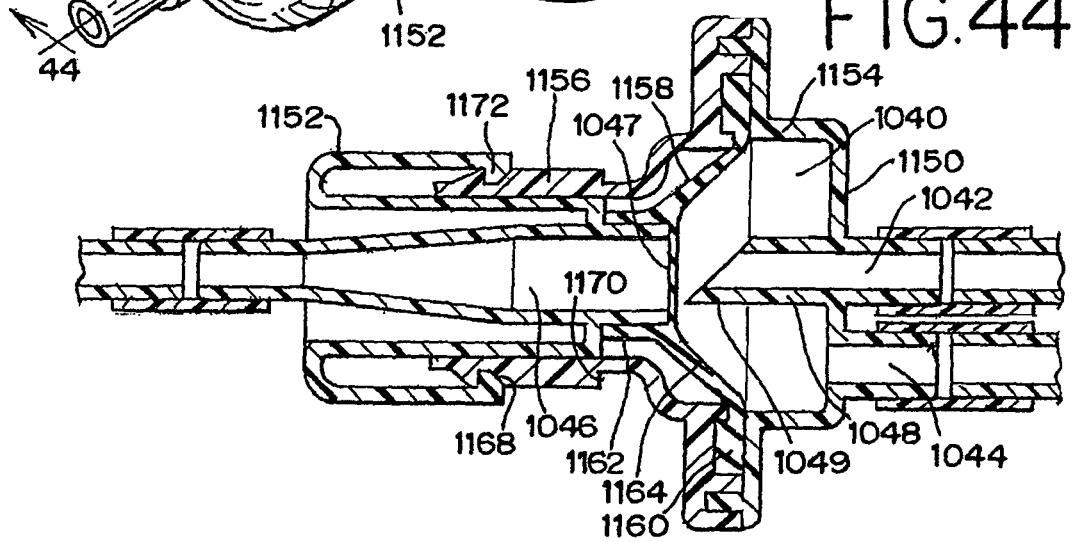
FIG. 44 is a cross sectional view of the flow controller of FIG. 43 in first position.
Figure 45:
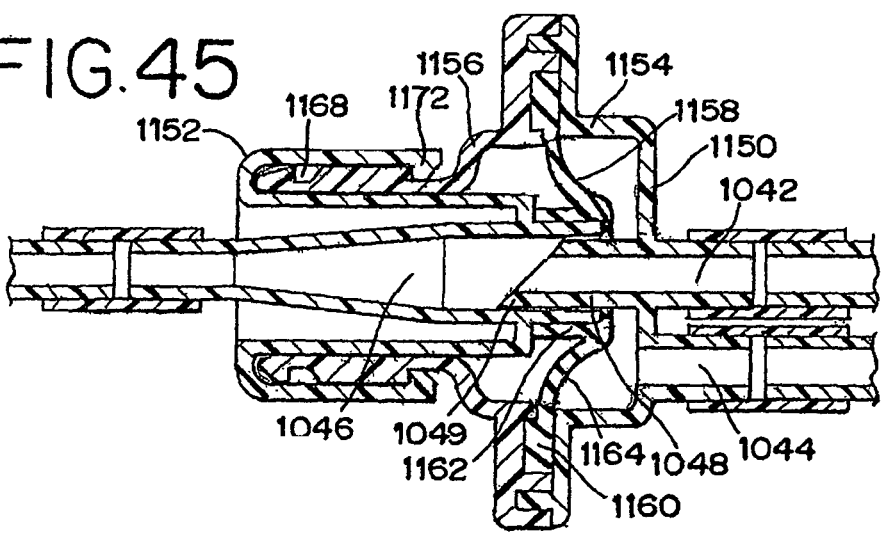
FIG. 45 is a cross sectional view of the flow controller of FIG. 43 in second position.

Rather than using an interference fit to hermetically seal the housing assembly 1038, the flow controller of the embodiment shown in FIGS. 40-42 utilizes a deformable bellows assembly 1158. The bellows assembly 1158 is preferably made of a vinyl material. The bellows assembly 1158 has a first end 1160 and a second end 1162 having a bellows portion 1164 therebetween. The first end 1160 is attached to the first housing assembly 1150. In this embodiment the first end 1160 is sealed between the body 1154 and the extension 1156. The second end 1162 is mounted on the end 1052 of the second outlet 1046. The second end includes a port that helps guide the access member 1048 into the second housing. FIGS. 43-45 illustrate another embodiment where the bellows assembly 1158 does not include a port.

The housing assembly 1038 is initially provided in a first position, illustrated in FIG. 41, wherein the extension 1156 of the first housing subassembly 1150 is inserted into the second housing subassembly 1152 to a point before the access member 1048 engages the sealing member 1047. In this position, fluid flows into the chamber 1040 from the inlet 1042 and exits the chamber 1040 through the first outlet 1044. The sealing member 1047 prevents fluid from flowing into the second outlet 1046 until desired.

To initiate fluid flow through the second outlet 1046, the housing assembly 1038 can be placed into a second position. FIG. 42 illustrates an example wherein the second outlet 1046 of the second housing subassembly 1152 is linearly advanced towards the first housing subassembly 1150. In this second position, fluid flow is established between the fluid inlet 1042 and the second outlet 1046 by the access member 1048 piercing the sealing member 1047 and entering the second outlet 1046. As the second outlet 1046 is advanced towards the inlet 1042 to achieve the second position, the bellows portion 1164 of the bellows assembly 1158 folds back towards the inlet 1042. The inlet 1042 and second outlet 1046 are aligned along a longitudinal axis in their respective housing subassemblies such that they can engage in this manner. In this configuration, fluid only flows from the inlet 1042 through the second outlet 1046. As illustrated in FIG. 42, fluid flow through the first outlet 1044 is prevented in the second position.

As mentioned above, the housing assembly 1038 may be provided with a locking mechanism to maintain the housing in the first and second positions. In this embodiment, the locking mechanism includes at least one latch and associated grooves. Extension 1156 defines grooves 1168, 1170 that removably receive latch 1172. When the housing assembly 1038 is in the first position, groove 1168 receives latch 1172. In order to place the housing assembly 1038 in the second position, the housing assembly 1036 is adapted to allow groove 1170 receives latch 1172.

Figure 46:
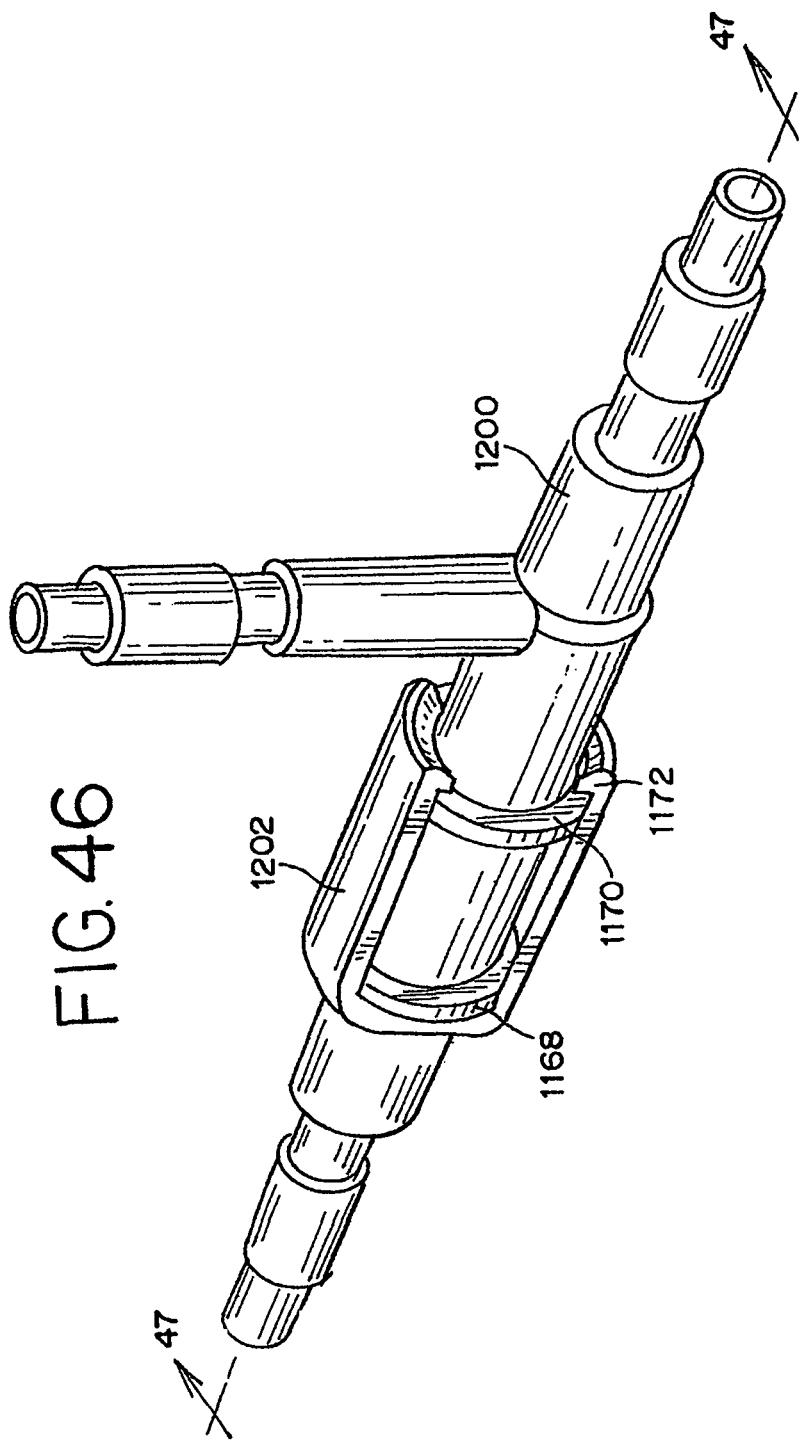
FIG. 46 is a perspective view of an additional embodiment of the flow controller.

FIGS. 46-48 illustrate another embodiment of the flow controller. The flow controller of FIGS. 46-48 is similar to the flow controllers of FIGS. 34-45 and similar or identical elements will be referred to with identical reference numerals.

As shown in FIGS. 46-48, the housing assembly 1038 includes a first housing subassembly 1200 and a second housing subassembly 1202. The first housing subassembly 1200 carries the inlet 1042 and first outlet 1044. The second housing subassembly 1202 carries the second outlet 1046. In this embodiment, the access member 1048 is a hollow channel that defines a piercing end 1049 and is defined on the end of the second outlet 1042.

A sealing member 1047 blocks the end 1052 of the second outlet 1046 to prevent fluid from flowing from the chamber 1040 into the second outlet 1046 until desired. In this embodiment, the sealing member 1047 is a hollow tube with one end closed by a membrane. The tube is positioned in the first housing subassembly 1200 to only block fluid flow into the second outlet 1046. The end of the tube with the membrane is positioned closest to the first outlet 1044.

The housing assembly 1038 is preferably initially provided in a first position, illustrated in FIG. 48, wherein the access member 1048 is inserted into first housing subassembly 1200 to a point before the access member 1048 engages the sealing member 1047. In this position, fluid flows into the chamber 1040 from the inlet 1042 and exits the chamber 1040 through the first outlet 1044. The sealing member 1047 prevents fluid from flowing into the second outlet 1046 until desired.

To initiate fluid flow through the second outlet 1046, the housing assembly 1038 can be placed into a second position. The first housing subassembly 1200 is preferably in a T-shape to aid the user in grasping and manipulating the flow controller 1036. The first outlet 1044 typically defines the base of the T. FIG. 47 illustrates an example wherein the second outlet 1046 of the second housing subassembly 1202 is linearly advanced even farther into the first housing subassembly 1200. In this position, fluid flow is established between the fluid inlet 1042 and the second outlet 1046 by the access member 1048 piercing the membrane of the end of the tube and entering the second outlet 1046. The inlet 1042 and second outlet 1046 are aligned along a longitudinal axis in their respective housing subassemblies such that they can engage in this manner. In this configuration, fluid only flows from the inlet 1042 through the second outlet 1046. As illustrated in FIG. 47, fluid flow through the first outlet 1044 is prevented in the second position.

Regardless of the position, the housing assembly 1038 is hermetically sealed. In the first position, the sealing member 1047 prevents fluid from escaping the housing assembly 1038. When in the second position, there is an interference fit between the access member 1048 and the second outlet 1046. However, the hermetic seal must be maintained during movement from the first position to the second position. As the access member 1048 is moved through the tube of the sealing membrane 1047 prior to piecing, the access member 1048 is sealed to the inner diameter of the tube of the sealing membrane 1047. In addition, a sealing ring 1204 may be added in order to maintain a hermetic seal during movement. In this embodiment, a sealing ring 1204 that interacts with the first housing subassembly 1200 is mounted on the exterior of the second outlet.

As mentioned above, the housing assembly 1038 may be provided with a lock mechanism to maintain the housing in the first and second positions. In this embodiment, the locking mechanism includes at least one latch and associated steps. The first housing subassembly 1200 defines steps 1168, 1170 that removably receive latch 1172. When the housing assembly 1038 is in the first position, step 1168 receives latch 1172. In order to place the housing assembly 1038 in the second position, the housing assembly 1036 is adapted to where step 1170 receives latch 1172.

FIGS. 49-51 illustrate an alternate embodiment of the flow controller. The flow controller of FIGS. 49-51 is similar to the flow controllers of FIGS. 46-48 but further includes a third housing subassembly 1206. Similar or identical elements will be referred to with identical reference numerals. As described previously, the flow controller 1038 generally includes a housing assembly 1038 which defines a chamber 1040 therein. The housing assembly 1038 includes an inlet 1042, a first outlet 1044, and a second outlet 1046. The end 1050 of the first outlet 1044 and the end 1052 of the second outlet 1046 are in fluid communication with the chamber 1040.

The third housing subassembly 1206 is attached on the first housing subassembly 1200. Preferably the third housing subassembly provides a cutout that interacts with the first outlet 1044 of the first housing assembly 1200. The third housing subassembly 1206 carries the steps 1168, 1170 of the locking mechanism. These steps 1168, 1170 interact with the latch 1172 on the second housing assembly 1202.

Figure 52:
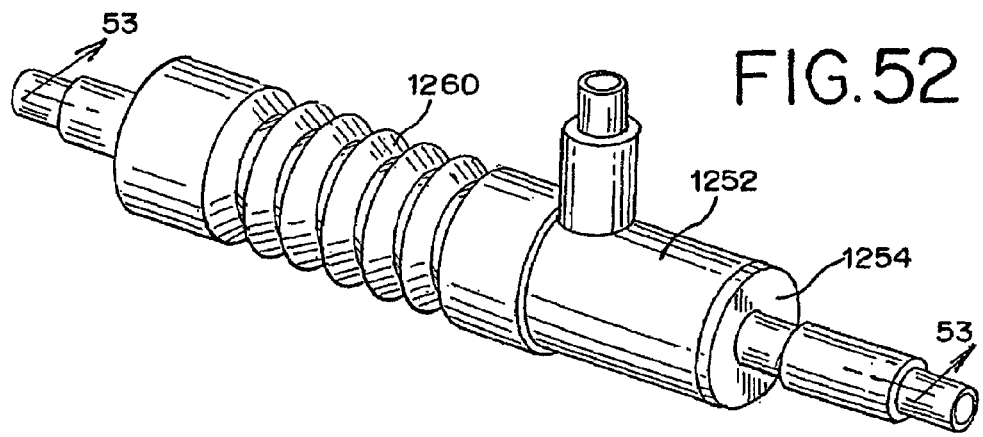
FIG. 52 is a perspective view of yet another embodiment of the flow controller.
Figure 53:
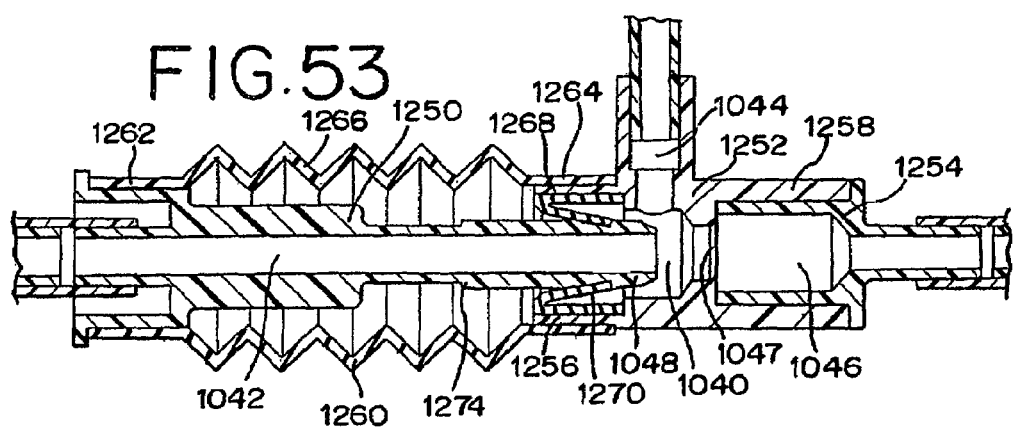
FIG. 53 is a cross sectional view of the flow controller of FIG. 52 in first position.
Figure 54:
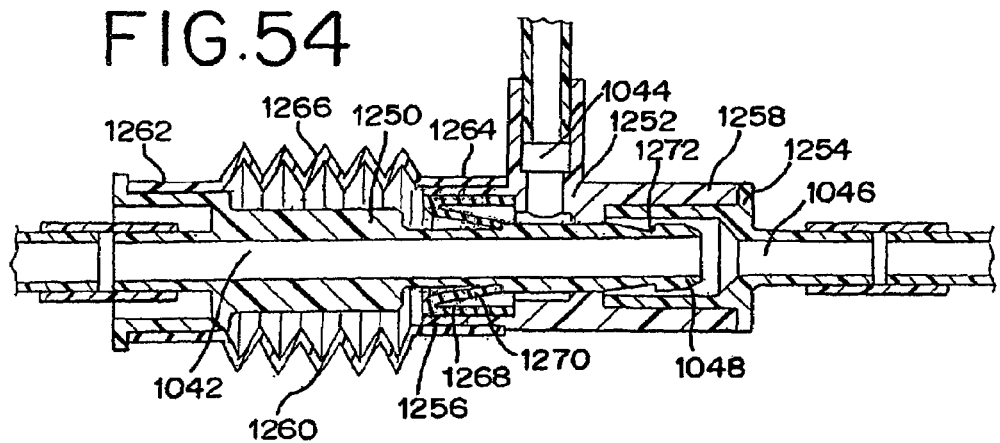
FIG. 54 is a cross sectional view of the flow controller of FIG. 52 in second position.

FIGS. 52-54 illustrate another embodiment of the flow controller. The flow controller of FIGS. 52-54 is similar to the flow controller of FIGS. 34-51 and similar or identical elements will be referred to with identical reference numerals.

The housing assembly 1038 includes three housing subassemblies. The first housing subassembly 1250 carries the inlet 1042. The second housing subassembly 1252 defines a chamber 1040 and carries the first outlet 1044, inlet port 1256 and second outlet port 1258. The third housing subassembly 1254 carries the second outlet 1046.

The three subassemblies are assembled such that inlet 1042 of the first housing subassembly 1250 is introduced into chamber 1040 through inlet port 1256 of second housing subassembly 1252 and second outlet 1046 of the third housing subassembly 1254 is introduced into second housing subassembly 1252 through second outlet port 1258. There is an interference fit between second outlet 1046 and second outlet port 1258.

A deformable bellows assembly 1260 links the first housing subassembly 1250 to the second housing subassembly 1252. The bellows assembly 1260 is preferably made of a vinyl material. The bellows assembly 1260 has a first end 1262 and a second end 1264 having a bellows portion 1266 therebetween. The first end 1262 is sealed to the first housing assembly 1250. The second end 1264 is sealed to the second housing assembly 1252. The inlet 1042 of the first housing assembly extends through the interior of the bellows assembly.

In this embodiment, the sealing member 1047 that prevents fluid flow into the second outlet 1046 is a membrane that is integrally formed as part of the second housing subassembly 1252. The access member 1048 is defined as part of the inlet 1042 and in this embodiment, the access member 1048 is a hollow channel with a flat end.

To alter fluid flow through the outlets, the housing assembly 1038 can be placed in first and second positions as previously discussed. Preferably, a locking mechanism is provided to constrain the housing in each position. In this embodiment, the locking mechanism is a ring 1268 positioned in the chamber 1040 of the second housing assembly 1252. The lock ring includes a finger 1270 that interacts with ridges 1272, 1274 on the inlet 1042 to hold the inlet in position. The finger 1270 prevents the inlet 1042 from being retracted out of the chamber 1040.

In the first position before the access member 1048 engages the sealing member 1047, the finger 1270 on the lock ring 1268 interacts with ridge 1272 on the inlet 1042. To initiate fluid flow through the second outlet 1046, the housing assembly 1038 is placed into a second position. In this position, fluid flow is established between the fluid inlet 1042 and the second outlet 1046 by the access member 1048 piercing the sealing member 1047 and entering the second outlet 1046. In this position, the finger 1270 on the lock ring 1268 is interacting with ridge 1274 and prevents the inlet 1042 from being retracted.

Figure 55:
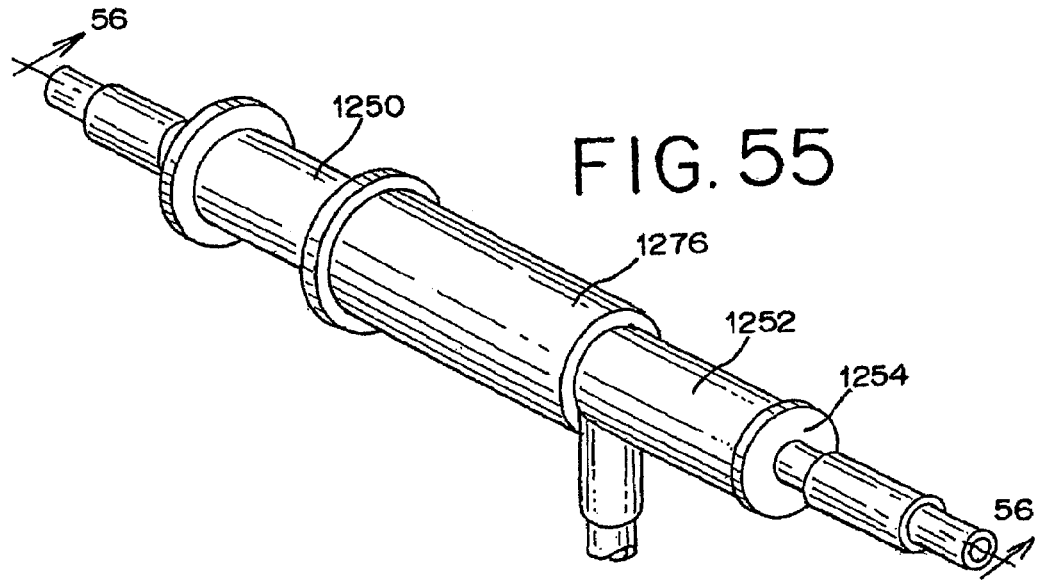
FIG. 55 is a perspective view of an alternative embodiment of the flow controller.
Figure 56:
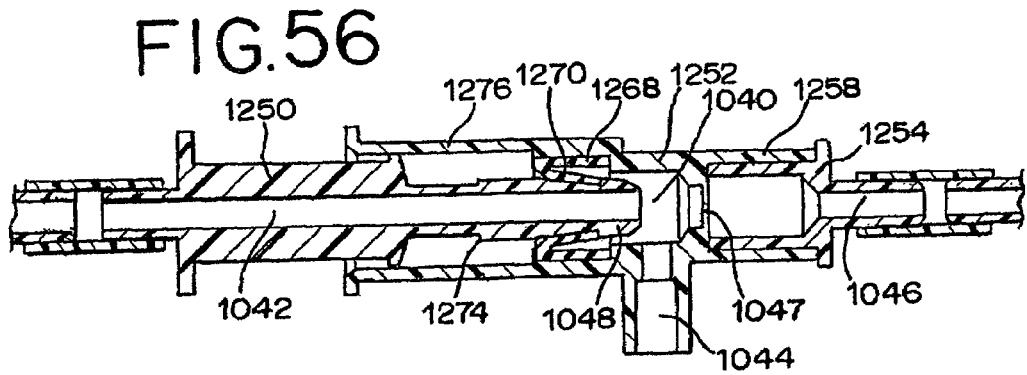
FIG. 56 is a cross sectional view of the flow controller of FIG. 55 in first position.
Figure 57:
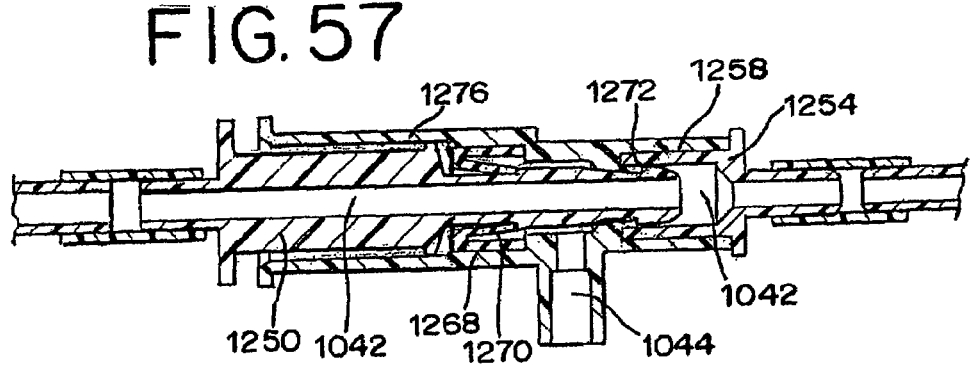
FIG. 57 is a cross sectional view of the flow controller of FIG. 55 in second position.

FIGS. 55-57 illustrate an alternate embodiment of the flow controller. The flow controller of FIGS. 55-57 is similar to the flow controller of FIGS. 52-54 but instead of a bellow's assembly 1260 the second housing subassembly 1252 includes an extension 1276. Similar or identical elements will be referred to with identical reference numerals.

In this embodiment, the second housing subassembly 1252 includes an extension 1276. Preferably, the extension is rigid coaxial wall; however, other members are suitable. The extension 1276 receives the first housing assembly 1250. In order to maintain a hermetic seal during movement, an interference fit is created between the extension 1276 and the first housing assembly 1250 as the first housing assembly 1250 is advanced into the second housing subassembly 1252.

Figure 58:
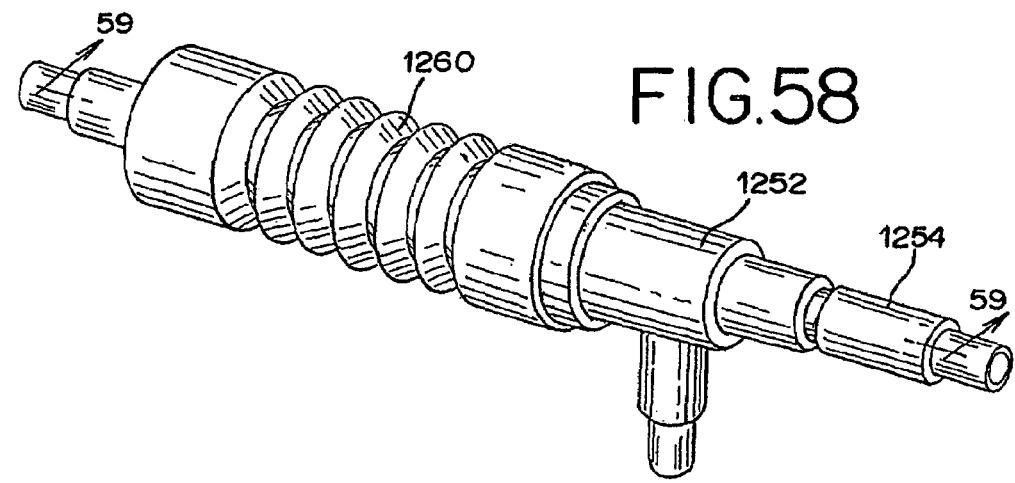
FIG. 58 is a perspective view of an additional embodiment of the flow controller.
Figure 59:
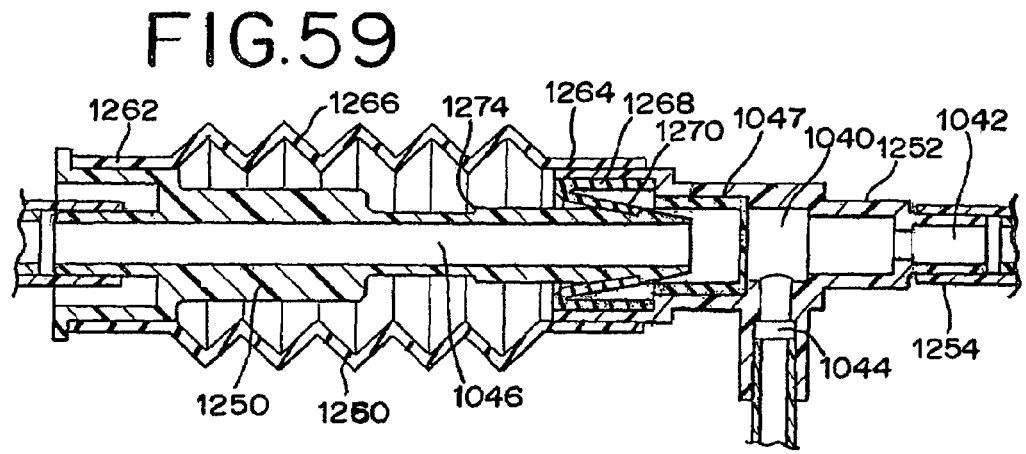
FIG. 59 is a cross sectional view of the flow controller of FIG. 58 in first position.
Figure 60:
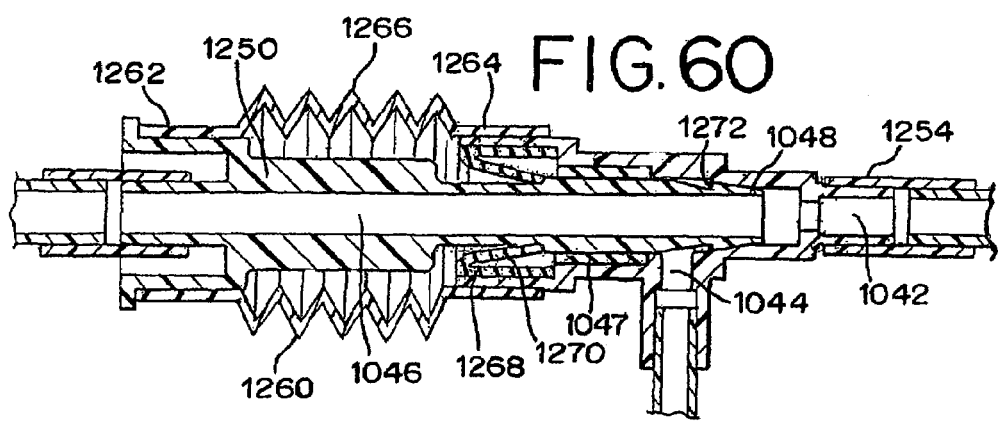
FIG. 60 is a cross sectional view of the flow controller of FIG. 58 in second position.

FIGS. 58-60 illustrate an alternate embodiment of the flow controller. The flow controller of FIGS. 58-60 is similar to the flow controller of FIGS. 52-54 but includes a separate sealing member 1047 rather than one that is integrally formed as part of the second housing. Additionally, the inlet 1042 and second outlets 1046 are on the other housing subassemblies. The second outlet 1046 is carried in the first housing subassembly 1250 and the inlet 1042 is carried in the third housing subassembly 1254. The access member 1048 is defined on the end of the second outlet 1046.

In this embodiment, the sealing member 1047 is a separate hollow tube with one end that is closed by a membrane. The tube is positioned in the chamber before the access member 1048 passes the first outlet 1044. The end of the tube with the membrane is positioned closest to the first outlet 1044. As the first housing subassembly 1250 is moved from the first position to the second, the second outlet 1046 interacts with the inner diameter of the tube to create a hermetic seal before the membrane is pierced. The access member 1048 then pierces the membrane and is advanced past the opening of the first outlet 1044 and into the inlet 1042 to create flow communication between the inlet 1042 and second outlet 1046.

Figure 61:
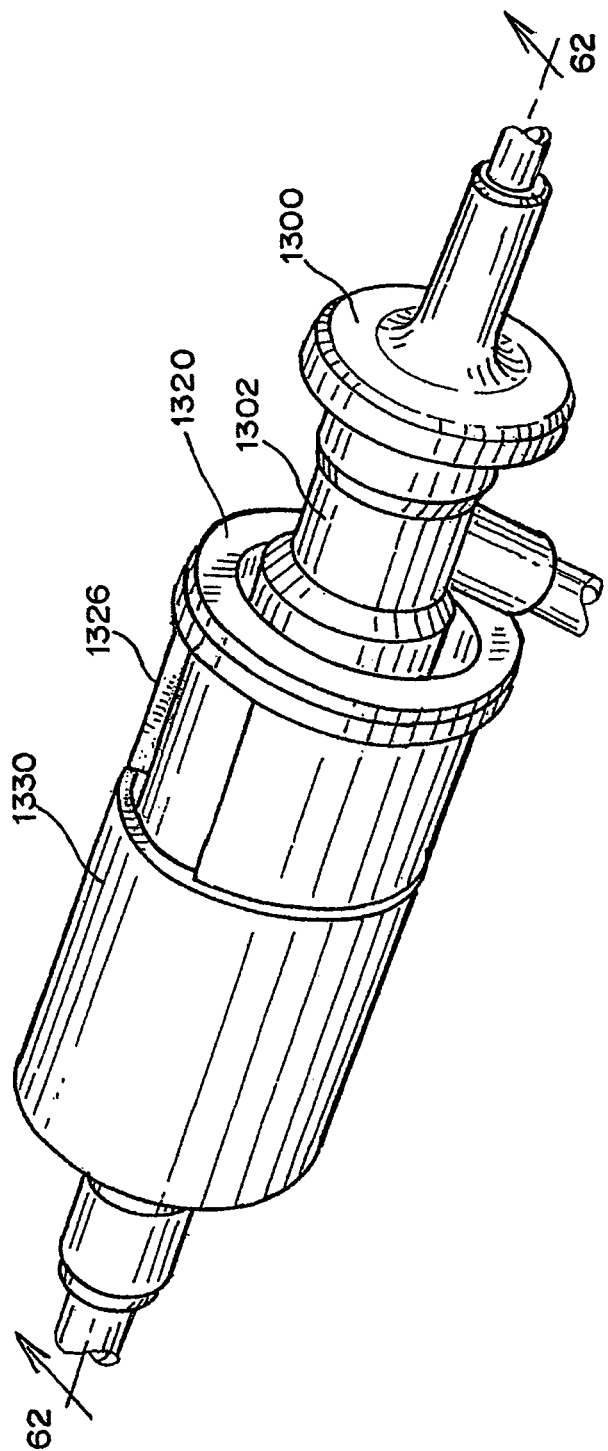
FIG. 61 is a perspective view of yet another embodiment of a flow controller.

FIGS. 61-63 disclose yet another embodiment of the flow controller of the present disclosure generally referred to with the reference numeral 1036. The flow controller of FIGS. 61-63 is similar to the flow controllers described above and similar or identical elements will be referred to with identical reference numerals.

The housing assembly 1038 includes three housing subassemblies. The first housing subassembly 1300 carries the inlet 1042. The second housing subassembly 1302 defines a chamber 1040 and carries the first outlet 1044, inlet port 1306 and second outlet port 1308. The third housing subassembly 1304 defines the second outlet 1046.

The three subassemblies are assembled such that the inlet 1042 of the first housing subassembly 1300 is introduced into the chamber 1040 through the inlet port 1306 of the second housing subassembly 1302 and the second outlet 1046 of the third housing subassembly 1304 is introduced into the second housing subassembly 1302 through the second outlet port 1308. There is an interference fit between the inlet 1042 and the inlet port 1306. The second housing subassembly 1302 defines the chamber 1040 where fluid flows from the inlet 1042 to the first outlet 1044.

In this embodiment, the access member 1048 is defined on the second outlet 1046. The access member 1048 is in the form of a hollow channel. In this embodiment, the sealing member 1047 is a membrane integrally formed as part of the second housing subassembly 1302.

Preferably, a lock ring 1310 interacts with the second and third housing subassemblies 1302, 1304. The lock ring 1310 mounts onto the second outlet port 1308 of the second housing subassembly 1302. The lock ring includes a finger 1312 that interacts with the third housing subassembly 1304 to maintain the housing assembly 1038 in certain positions.

In the first position, where the second outlet 1046 is inserted into second housing assembly 1302 to a point before the access member 1048 engages the sealing member 1047, the finger 1312 on the lock ring 1310 interacts with ridge 1314 on the second outlet 1046. To initiate fluid flow through the second outlet 1046, the housing assembly 1038 is placed into a second position. In this position, fluid flow is established between the fluid inlet 1042 and the second outlet 1046 by the access member 1048 piercing the sealing member 1047 and entering the inlet 1042. In this position, the finger 1312 on the lock ring 1310 interacts with ridge 1316 and prevents the second outlet 1046 from being retracted.

Rather than using an interference fit to seal the housing assembly, the flow controller utilizes a deformable bellows assembly 1318. The bellows assembly 1318 is preferably made of a vinyl material. The bellows assembly 1318 has a first end 1320 and a second end 1322 having a bellows portion 1324 therebetween. The first end 1320 is connected to the end of the third housing subassembly 1304. The second end 1322 is mounted on the lock ring 1310. As the second outlet 1046 is advanced towards the inlet 1042 to achieve the second position, the bellows portion 1324 of the bellows assembly 1318 folds in accordion-like fashion.

In order to vent air during movement between positions, the third housing subassembly 1304 defines at least one opening. These openings 1328 are positioned along the third housing subassembly such that they are blocked by the lock ring 1310 once the access member 1048 pierces the sealing member 1047. When not blocked, the openings 1328 allow air from inside the bellows assembly 318 to be vented through the second outlet 1046 as the bellows assembly 1318 is collapsed.

In order to prevent damage to the bellows assembly 1318, preferably, a cover 1330 may be slidably mounted on the bellows assembly 1318. The cover 1330 is typically a rigid, hollow member that protects the bellows assembly 1318 and also provides a gripping portion for the user. Preferably, when the housing assembly 1038 is in the first position, the cover 1330 only covers the first end 1320 and bellows portion 1324 of the bellows assembly 1318. As the housing assembly 1038 is adapted to the second position the cover 1330 slides along the second end 1322 of the bellows assembly 1318.

In addition, a lock mechanism 1326 may be included to prevent the housing assembly from adapting to the second position. The lock mechanism 1326 is preferably a removable ring that is mounted on the second end 1322 of the bellows assembly 1318. The ring prevents the cover from sliding down the second end 1322 of the bellows assembly 1318. Thus, movement of the housing assembly 1038 to the second position is prevented until the ring is removed.

FIGS. 66-69 disclose another embodiment of the flow controller. The flow controller of FIGS. 66-69 is similar to the flow controller of FIGS. 34-65 and similar or identical elements will be referred to with identical reference numerals.

In this embodiment, the flow controller has a housing assembly 1038 which defines a chamber 1040 therein. The housing assembly 1038 is adapted to be located inside a container 1400. However, in one embodiment illustrated in FIG. 66, the housing assembly 1038 is adapted to be mounted on the container 1400. The container 1400 is preferably a standard flexible plastic bag as is typically used throughout the medical field to store biological fluid. The container 1400 is typically provided to collect a sample of biological fluid before collecting the "main" collection of fluid. The container 1400 may typically hold approximately 50 ml of fluid, or a sufficient amount to provide an adequate sample size.

The housing assembly 1038 defines an inlet 1042, first outlet 1044 and second outlet 1046. The inlet 1042 and second outlet 1046 are preferably adapted for connection with flexible tubing according to known construction. The inlet 1042 is in flow communication with a fluid source, such as a donor, typically by a venous access device such as phlebotomy needle, while the second outlet 1046 is communicable with a separate collection zone, preferably a main collection container (not shown). Inlet 1042 and second outlet 1046 are preferably coaxial and have minimal fluid flow resistance to avoid hemolysis, clotting and "quantity not sufficient" collections.

Figure 67:
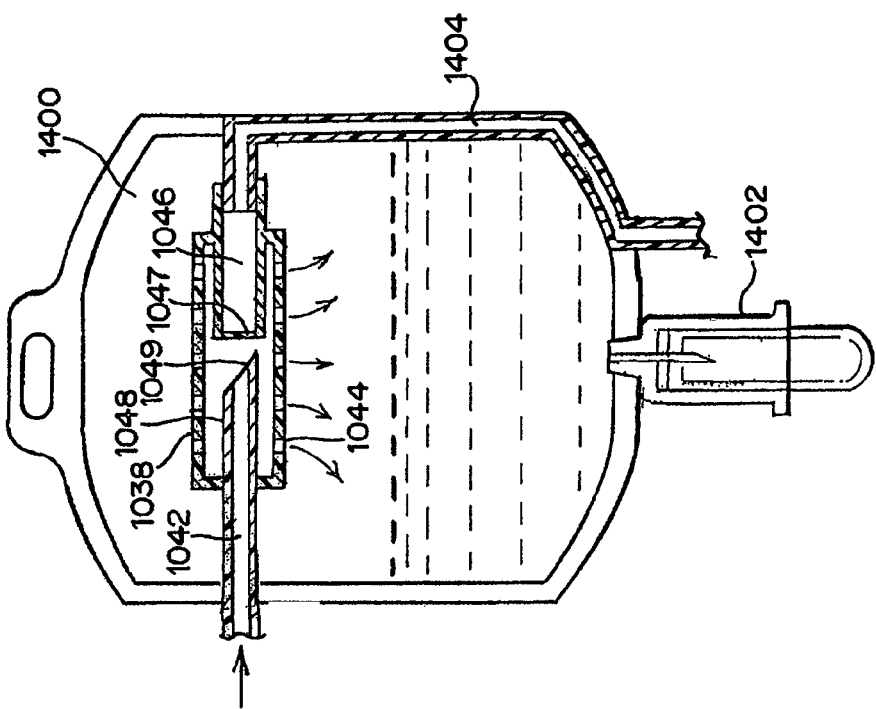
FIG. 67 is a perspective view of yet another embodiment of the flow controller in first position.
Figure 66:
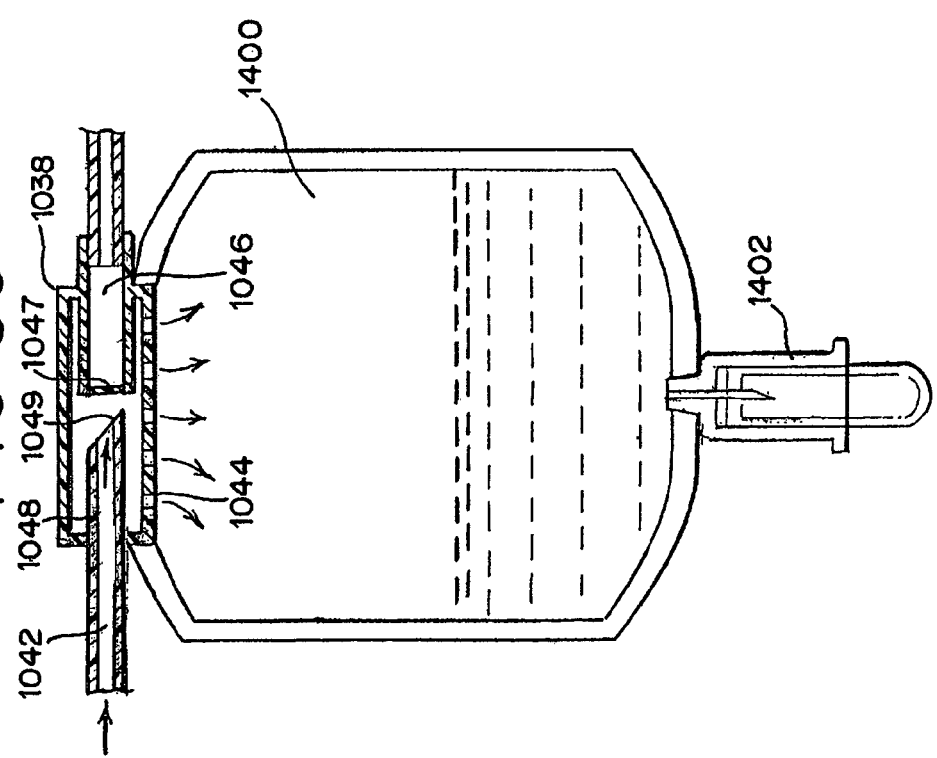
FIG. 66 is a perspective view of another embodiment of the flow controller in first position.

In an embodiment illustrated in FIG. 67, the flow path extending from the second outlet 46 is integrally formed as part of the container such as by forming an interior seal. In this embodiment, the access member 1048 is defined or otherwise provided on the end of the inlet 1042 and is a hollow channel preferably provided with a piercing end 1049. The housing assembly 1038 helps prevent the access member 1048 from puncturing the container 1400. A sealing member 1047 blocks the end 1052 of the second outlet 1046 to prevent fluid from flowing from the chamber 1040 into the second outlet until desired. In this embodiment, the sealing member 1047 is a membrane located between second outlet 1046 and access member 1048 or is preferably joined to the end of the second outlet 1046 to prevent fluid flow therein until desired. In this embodiment, the first outlet 1046 is defined as a plurality of apertures distributed on the housing assembly 1038. Of course, a number of other structures are possible to allow fluid to flow from the chamber 1040 into the container.

Figure 68:
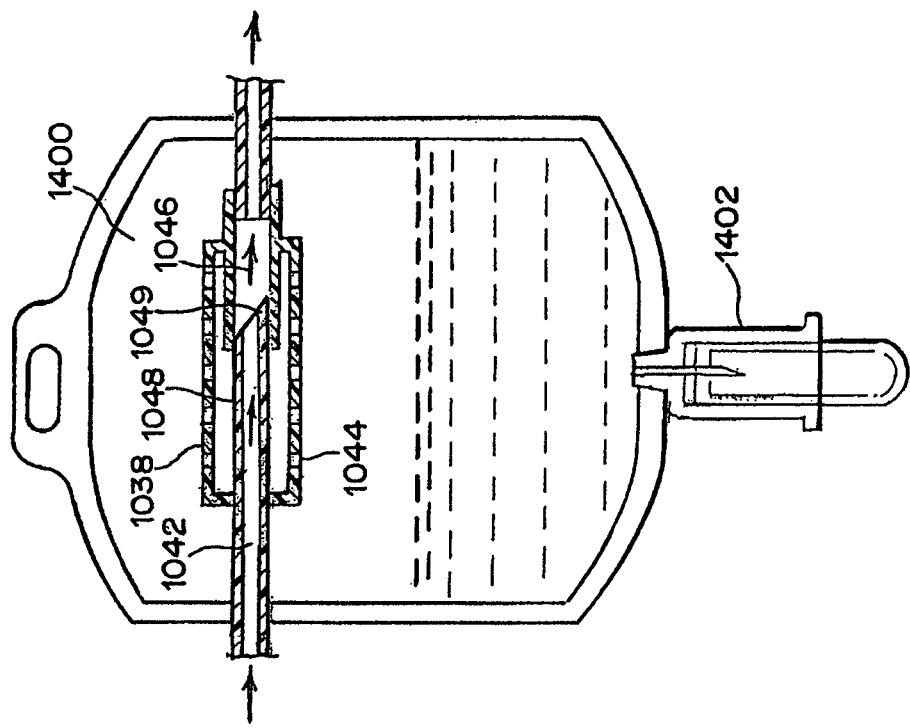
FIG. 68 is a perspective view of an alternative embodiment of the flow controller in first position.

In another embodiment shown in FIG. 68 the housing assembly 1038 of the flow controller 1036 is preferably initially provided in a first position wherein the access member 1048 is disposed in the housing assembly 1038 at a point before the access member 1048 engages the sealing member 1047. Preferably, the access member 1048 is positioned very close to the sealing member 1047. This reduces the stroke length or distance the access member 1048 must travel to engage the sealing member 1047 in the second position. As shown in FIG. 68, in first position, fluid flows into the chamber 1040 through the inlet 1042 and exits the chamber 1040 through the first outlet 1044 openings. The sealing member 1047 prevents fluid from flowing into the second outlet 1046.

Figure 69:
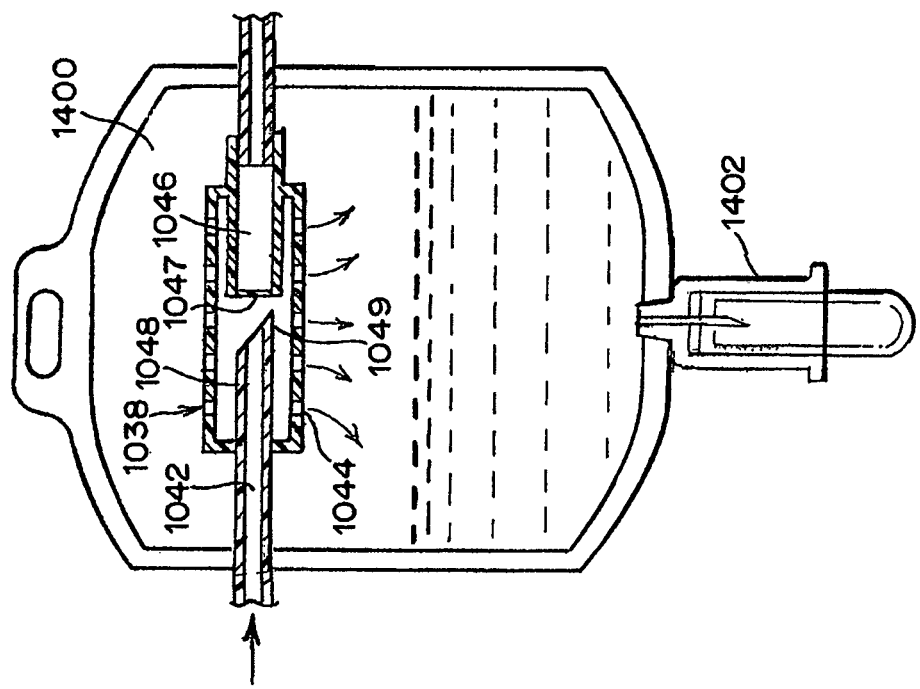
FIG. 69 is a perspective view of the embodiment of the flow controller in second position.

To initiate fluid flow through the second outlet 1046, the housing assembly 1038 can be placed into a second position. In this position illustrated in FIG. 69, fluid flow is established between the inlet 1042 and the second outlet 1046 by the access member 1048 engaging (e.g., by piercing) the sealing member 1047 and entering the second outlet 1046. The end of the access member 1048 experiences a friction fit as it engages second outlet 1046. The inlet 1042 and the second outlet 1046 are aligned along a longitudinal axis such that they can engage in this manner. In this configuration, fluid only flows from the inlet 1042 through the second outlet 1046. As illustrated in FIG. 69, fluid flow through the first outlet 1044 is prevented in the second position.

To take a sample of fluid from the container, preferably, a sampling device 1402 may be associated with the container. In this embodiment, the sampling device is in the form of a sample tube holder of known construction. As is typical, sample tube holder includes a hollow barrel for receiving a vacuum sealed tube or vial. A needle within the barrel pierces the rubber cap of the sample vial, thereby introducing blood therein.

The embodiments of flow controllers and flow control assemblies described above may be used in a closed position that restricts fluid flow from a container of liquid while the container is in storage (i.e., a bag of saline fluid or blood in a hospital). Also, the flow controllers may be used to restrict fluid flow in containers of liquid stored for a long period of time (i.e., 2 years). Further, the non-frangible flow controllers described above may be closed after opening to once again restrict fluid flow.

It will be understood that there are numerous modifications of the illustrated embodiments described above which will be readily apparent to one skilled in the art, such as many variations and modifications of the interleaved contact and/or its components including combinations of features disclosed herein that are individually disclosed or claimed herein, explicitly including additional combinations of such features, or alternatively other types of interleaved contacts. Also, there are many possible variations in the materials and configurations. These modifications and/or combinations fall within the art to which this invention relates and are intended to be within the scope of the claims, which follow.

What is claimed is:

1. A fluid flow controller comprising:
a unitary housing having a longitudinal axis and an axial length with a first end and a second end, said housing including first and second finger-gripping portions integral with a central portion disposed between said finger-gripping portions, said finger-gripping and central portions defined by a continuous, integrally molded housing wall;
wherein each of said finger-gripping portions and said central portion define an outermost surface, and wherein said outermost surface of said housing finger-gripping portions extends radially outwardly of the outermost surface of said central portion,
said housing further defining an interior flow path and including a breakable member at least partially positioned within said flow path of the housing to prevent the passage of fluid through the flow path;
wherein said housing wall at said central portion has a selected thickness and said housing wall at each of said finger-gripping portions has a wall thickness that is greater than said wall thickness of said housing at said central portion; and
wherein each of said finger-gripping portions extends entirely around the longitudinal axis of said housing and has a cross-section that is generally square-shaped with rounded corners and a concave finger-contacting surface when viewed in a plane that is perpendicular to said longitudinal axis.

2. The fluid flow controller of claim 1 wherein the selected thickness of said central portion is between about 0.005 inches to about 0.04 inches.

3. The fluid flow controller of claim 1 wherein the breakable member further comprises at least one set of projections extending radially outwardly from said breakable member.

4. The fluid flow controller of claim 1 wherein the finger-gripping portions further include a textured or contoured exterior surface.

5. The fluid flow controller of claim 1 wherein the first and second finger-gripping portions are axially spaced.

6. The fluid flow controller of claim 1 further comprising an inlet port at said first end and an outlet port at said second end.

7. The fluid flow controller of claim 6 wherein each of said finger-gripping portions is located between said central portion and said inlet and outlet ports, respectively.

8. A fluid flow control system comprising:
a first fluid source;
a first fluid flow path in fluid communication with the first fluid source;
a flow controller comprising a unitary housing having a longitudinal axis and an axial length with a first end and a second end, said housing including first and second finger-gripping portions integral with a central portion disposed between said finger-gripping portions, said finger-gripping and central portions defined by a continuous, interally molded housing wall
wherein each of said finger-gripping portions and said central portion define an outermost surface, and wherein said outermost surface of said housing finger-gripping portions extends radially outwardly of the outermost surface of said central portion,
said housing further defining an interior flow path for receiving fluid from the first fluid flow path and including a breakable member comprising a stem integrally molded to a tubular member at least partially positioned within an interior flow path of the housing to prevent the passage of fluid through the flow path;
wherein said housing wall at said central portion comprising a wall having has a selected thickness and said housing wall at each of said finger-gripping portions has a wall thickness that is greater than said wall thickness of said housing at said central portion; and
wherein each of said finger-gripping portions extends entirely around the longitudinal axis of said housing and has a cross-section that is generally square-shaped with rounded corners and a concave finger-contacting surface when viewed in a plane that is perpendicular to said longitudinal axis;
a second fluid flow path in communication with said housing when the stem of the breakable member is separated from the tubular member;
a container in fluid communication with said second fluid flow path.

* * * * *